US010962451B2

(12) United States Patent
Joseph, Jr.

(10) Patent No.: US 10,962,451 B2
(45) Date of Patent: Mar. 30, 2021

(54) CONDENSATE REMOVAL APPARATUS FOR SAMPLING

(71) Applicant: ENVIROLYTICS, LLC, Olympia, WA (US)

(72) Inventor: Alan W. Joseph, Jr., Olympia, WA (US)

(73) Assignee: Envirolytics, LLC, Olympia, WA (US)

( * ) Notice: Subject to any disclaimer, the term of this patent is extended or adjusted under 35 U.S.C. 154(b) by 285 days.

(21) Appl. No.: 15/853,075

(22) Filed: Dec. 22, 2017

(65) Prior Publication Data

US 2018/0180518 A1 Jun. 28, 2018

Related U.S. Application Data

(60) Provisional application No. 62/437,917, filed on Dec. 22, 2016.

(51) Int. Cl.
*G01N 1/22* (2006.01)
*G01N 1/44* (2006.01)
(Continued)

(52) U.S. Cl.
CPC ............ *G01N 1/2273* (2013.01); *B60K 11/02* (2013.01); *B60K 11/04* (2013.01); *F01P 3/20* (2013.01);
(Continued)

(58) Field of Classification Search
CPC ... B60K 11/02; B60K 11/04; B60Y 2200/147; B60Y 2400/432; B60Y 2400/433;
(Continued)

(56) References Cited

U.S. PATENT DOCUMENTS 3,730,001 A 5/1973 Goodwin
4,093,945 A 6/1978 Collier et al.
(Continued)

FOREIGN PATENT DOCUMENTS

WO 2017069979 A1 4/2017

OTHER PUBLICATIONS

Non-Final Office Action for U.S. Appl. No. 15/852,967 dated Jul. 29, 2019, 6 pages.
(Continued)

*Primary Examiner* — Nimeshkumar D Patel
*Assistant Examiner* — Gedeon M Kidanu
(74) *Attorney, Agent, or Firm* — John F. Rollins

(57) ABSTRACT

Systems, devices, and methods are described herein for an auxiliary heat exchange system for use in scientific sampling. In one aspect, a heat exchange system may include at least one first conduit housed in an external casing, that is removably attachable to a heat/cooling system of a vehicle. Another conduit, such as a tracer tube, may be positioned proximate to the first conduit and housed in the external casing for at least a partial length of the first conduit. The tracer conduit may include a first end that is removably attachable to a gas collection device and a second end removably attachable to a measuring device. The first conduit may be configured to carry heated liquid from the heating/cooling system of the vehicle to maintain at least a threshold temperature of gas samples in the tracer conduit to prevent or reduce the formation of condensates in the tracer conduit.

24 Claims, 23 Drawing Sheets

Engine
Alternater 118
100
102
106
104
112
Inverter #1 108
Inverter #2 110
112
114
116
118
Charge Controller
128
Low-Voltage Control Panel
GPS Unit 122
Weather Station 124
Other 12V Sensors 126
Wind Generator

(51) Int. Cl.

| | |
|---|---|
| ***B60K 11/04*** | (2006.01) |
| ***F01P 3/20*** | (2006.01) |
| ***B60K 11/02*** | (2006.01) |
| ***G01N 33/00*** | (2006.01) |
| ***F01P 7/16*** | (2006.01) |
| ***G01N 30/88*** | (2006.01) |
| ***G01N 30/72*** | (2006.01) |
| ***G01N 35/00*** | (2006.01) |
| ***F01P 11/16*** | (2006.01) |

(52) U.S. Cl.
CPC ........... *G01N 1/44* (2013.01); *G01N 33/0016* (2013.01); *B60Y 2200/147* (2013.01); *B60Y 2400/432* (2013.01); *B60Y 2400/433* (2013.01); *F01P 7/16* (2013.01); *F01P 11/16* (2013.01); *G01N 30/72* (2013.01); *G01N 30/88* (2013.01); *G01N 33/0047* (2013.01); *G01N 2001/2288* (2013.01); *G01N 2035/00475* (2013.01)

(58) Field of Classification Search
CPC ..... F01P 11/16; F01P 3/20; F01P 7/16; G01N 1/2273; G01N 1/44; G01N 2001/2288; G01N 2035/00475; G01N 30/72; G01N 30/88; G01N 33/0016; G01N 33/0047
See application file for complete search history.

(56) References Cited

U.S. PATENT DOCUMENTS

| | | | | |
|---|---|---|---|---|
| 4,863,602 | A | 9/1989 | Johnson | |
| 5,675,233 | A | 10/1997 | Kaneko et al. | |
| 5,960,898 | A | 10/1999 | Okada et al. | |
| 6,021,678 | A | 2/2000 | Vardiman et al. | |
| 6,042,634 | A * | 3/2000 | Van Tassel | G01N 1/2258 95/117 |
| 6,079,629 | A * | 6/2000 | Morikawa | B60H 1/2206 237/12.3 C |
| 6,116,098 | A | 9/2000 | Lubek et al. | |
| 6,154,658 | A | 11/2000 | Caci | |
| 9,752,514 | B2 * | 9/2017 | Amaral | F02D 19/0605 |
| 2003/0081935 | A1 | 5/2003 | Kirmuss | |
| 2004/0025516 | A1 * | 2/2004 | Van Winkle | F25B 21/04 62/3.3 |
| 2004/0121479 | A1 | 6/2004 | Chen et al. | |
| 2004/0157342 | A1 | 8/2004 | Lovell et al. | |
| 2004/0200265 | A1 | 10/2004 | Eden et al. | |
| 2004/0221577 | A1 * | 11/2004 | Yamaguchi | F01P 3/20 60/520 |
| 2005/0056785 | A1 | 3/2005 | Chou et al. | |
| 2005/0093508 | A1 | 5/2005 | Taniguchi et al. | |
| 2006/0066105 | A1 | 3/2006 | Johnson et al. | |
| 2008/0007728 | A1 | 1/2008 | Schneider et al. | |
| 2010/0165593 | A1 | 7/2010 | Townsend et al. | |
| 2012/0135537 | A1 | 5/2012 | Horton et al. | |
| 2012/0267540 | A1 | 10/2012 | Frank | |
| 2012/0273177 | A1 * | 11/2012 | Kim | F01M 5/002 165/164 |
| 2013/0196104 | A1 * | 8/2013 | Matsumoto | C08L 79/08 428/36.92 |
| 2014/0202430 | A1 | 7/2014 | Monros | |
| 2015/0330868 | A1 | 11/2015 | Fukami et al. | |
| 2016/0017822 | A1 * | 1/2016 | Amaral | F02M 31/14 123/557 |
| 2016/0081587 | A1 | 3/2016 | Ghazarian | |
| 2016/0137208 | A1 | 5/2016 | Powers et al. | |
| 2017/0072808 | A1 | 3/2017 | Caldeira et al. | |
| 2017/0335805 | A1 * | 11/2017 | Zhang | F01N 3/20 |
| 2018/0329108 | A1 | 11/2018 | Gonsky, Jr. et al. | |

OTHER PUBLICATIONS

International Preliminary Report on Patentability for Application No. PCT/US2017/068241, dated Mar. 8, 2019, 4 pages.
International Search Report and Written Opinion for PCT/US2017/068241, dated Mar. 12, 2018, 13 pages.
Final Office Action for co-pending U.S. Appl. No. 15/852,967, dated Jan. 13, 2020, 6 pages.

* cited by examiner

CONDENSATE REMOVAL APPARATUS FOR SAMPLING

PRIORITY CLAIM

This application claims the benefit of and priority from U.S. Provisional Application No. 62/437,917 filed Dec. 22, 2016; which application and contents thereof is hereby incorporated by reference in its entirety as if fully set forth herein.

FIELD OF DISCLOSURE

The present disclosure is directed to scientific measuring platforms and devices, and more specifically to systems and devices for removing condensate from collected samples.

BACKGROUND

Prior approaches to air sampling have been plagued with non-constant temperatures or cold spots in the transport line or tracer tube that delivers samples to measuring equipment, thus leading to condensation. The longer the transport line or tracer tube, the more chance for condensate formation. Condensation may contaminate the interior of the tracer tube, which can cause artificially elevated background signals (or other inaccuracies) in the scientific equipment. These condensates must then be "baked out" of the sampling system, in order to obtain valid measurements, causing equipment and measurement downtime. Moreover, when condensates traveling in the tracer tube reach the scientific measuring equipment (such as a mass spectrometer), expensive decontamination, tracer tube replacement, and long equipment down times can result. As a result, improvements can be made to air and gas transport systems, used for scientific measurement and analysis.

SUMMARY

The present disclosure is directed to systems, devices, and methods for a mobile scientific or measuring platform. In one aspect, a mobile scientific platform may include a vehicle having an electric energy source and a measuring device, such as a mass spectrometer, coupled to the electric energy source. An input line may be coupled to the measuring device and one or more sample collectors, for example, for obtaining gas samples. In some aspects, the input line may include a heating element configured to maintain a line temperature that is equal to or above the temperature of the samples collected, to reduce or prevent the formation of condensates in collected samples. In some aspects, the mobile scientific platform may run, or be switched to run, on electric, propone, compressed natural gas, or other similar fuel to enable the collection of gas samples free of (or having reduced levels of) vehicle caused contamination.

In some aspects, the vehicle may include a propulsion source, such as a combustion engine. The propulsion source can be operated using at least one of gas or diesel fuel or other similar fuel. In some cases, the propulsion source can be switched to operate using at least one of propane, compressed natural gas, electric, or other reduced emissions fuel or energy source. This may be particularly useful when the mobile scientific platform is used to obtain gas samples while moving, to avoid contaminating the gas samples obtained. In some examples, the platform may include a switch operable to switch the source of fuel of the propulsion source from gasoline or diesel to propane or compressed natural gas or electric based on whether the measuring device is receiving a sample from the input line.

In some aspects, the propulsion source of the vehicle may include a cooling system. In this scenario, the input line may be coupled (e.g., removably coupled) to the cooling system. The input line may include a sample tube and the heating element may include two heating tubes each adjacent to the sample tube. The two heating tubes may be removably coupled to the cooling system to carry heated coolant from the heating/cooling system, to maintain a threshold temperature of the samples in the sample tube.

In some examples, the mobile platform may include a trailer removably coupled to the vehicle, wherein the trailer houses at least a part of the electric power source. In some cases, the vehicle may include a propulsion source, which may be switchable between operating on gas or diesel fuel to propane, compressed natural gas, electric, or other reduced-emissions sources. In this scenario, the trailer may house the propane or compressed natural gas or another alternative fuel. In some examples, the electric power source may include an array of batteries configured to provide continuous operational power to the measuring device for at least twelve hours.

Some aspects may include a method of collecting air samples for measurement utilizing a mobile platform. The method may include detecting that a measuring device removably attached to a mobile platform is active. Based on the detecting, propulsion source of the vehicle may be switched to one of propane, compressed natural gas, or electric. The method may further include obtaining an air sample using a sample collector that is coupled to the measuring device, and analyzing the sample and generating a notification based on the analyzing. By switching (or alternatively only running on) alternative fuels, samples for measurement may be obtained without contaminates caused by emissions originating from the vehicle.

In some cases, the obtaining the air samples may further include obtaining the air sample via a supply line that is coupled to the measuring device. In some cases, obtaining the air sample may include maintaining a minimum temperature of the air sample in the supply line using liquid coolant obtained from a cooling system of the propulsion source of the vehicle. In some aspects, the liquid coolant may run adjacent to an air sample tube of the supply line. In some examples, obtaining the air sample may include obtaining the air sample with a vapor collector, wherein the vapor collector includes a first and second hollow tube each having perforations, and wherein the first tube is positioned at least partially inside the second tube such that the perforations of the first and second hollow tubes do not overlap.

In another aspect, a portable scientific platform may include a mobile vehicle, a sampling device coupled to the mobile vehicle for taking a gas sample. The platform may additionally include a de-condensation device for removing condensation from the gas sample and outputting a processed sample. The platform may also include an analysis device for analyzing the processed sample.

In some aspects, the mobile vehicle includes a propulsion source, which does not contaminate the gas sample(s), for example, when the propulsion source is active. In some cases, the mobile vehicle is switchable from operating on a contaminating propulsion source to a non-contaminating propulsion source, to enable taking a contaminant-free gas sample while the vehicle is moving.

In some cases, the sample device includes a two layered filtering device, with each layer have perforations that do not overlap. In some aspects, the two layers each form a tube that is closed at a common end. In yet some cases, the de-condensation device concludes a supply line that is heated to at or above an ambient temperature of the gas sample taken, for example, to prevent or reduce contamination of the samples by condensates. In some cases, the heating element includes two lines adjacent to a sample line, wherein the two lines carry heated coolant from a heating/cooling system of the vehicle.

Systems, devices, and methods are also described herein for an auxiliary heat exchange system for use in scientific sampling. In one aspect, a heat exchange system may include at least one first conduit or process tube housed in an external casing, that is removably attachable to a heat/cooling system of a vehicle. Another conduit, such as a tracer tube, may be positioned proximate to the first conduit and housed in the external casing for at least a partial length of the first conduit. The tracer conduit may include a first end that is removably attachable to a gas collection device and a second end removably attachable to a measuring device. The first conduit may be configured to carry heated liquid from the heating/cooling system of the vehicle to maintain at least a threshold temperature of gas samples in the tracer conduit to prevent or reduce the formation of condensates in the tracer conduit.

In some cases, the heat exchange system may include two conduits or process tubes each positioned parallel to the tracer conduit in the external casing. In some cases, the first conduit and the second conduit may be in direct contact with the tracer conduit. In some examples the first conduit, the second conduit, and/or the tracer conduit may be made of PFA, PEEK, or PTFE. In some examples, the first conduit, the second conduit, and/or the tracer conduit may be incased in water soluble chloride in absorption-resistant fibrous glass insulation. The external casing may include a non-halogenated thermoplastic urethane that covers the absorption-resistant fibrous glass insulation.

In some aspects, the first conduit, and in some cases the second conduit, forms an axillary loop with a heating circuit of the heating/cooling system of the vehicle. In one example, the first conduit, and in some cases the second conduit, may be removably attachable to an inlet heating hose providing liquid to a heater core of the vehicle and an outlet heating hose providing liquid back to the heating/cooling system of the vehicle. In another example, the first conduit, and in some cases the second conduit, may be removably attachable to radiator hose of the heating/cooling system and to a coolant expansion tank of the heating/cooling system of the vehicle. In some cases, the auxiliary heat exchange system may include an auxiliary pump coupled to the at least one first conduit, wherein the pump is configured to move liquid through an extended length of the first conduit.

In some aspects, the gas collection device may include a two layered filtering device, wherein the two layers each have perforations that do not overlap. In some cases, the two layers each form a tube that is closed at a common end.

In some aspects, the threshold temperature may be set to greater than an ambient temperature of the gas samples. In some aspects, the vehicle includes a mobile scientific platform.

Systems, devices, and methods are also described herein for a vapor or gas sampling device. In one aspect, the described collector may include an outer vapor collector or outer tube having first and second ends, with the hollow tube forming a plurality of perforations proximate to the first end. In some examples, the perforations may prevent the passing of detritus or environmental contaminants through the perforations. The collector may also include an inner vapor collector or inner tube having a first end and a second end, with the hollow tube forming a plurality of perforations proximate to the second end, which is opposite the first end of the outer tube. The inner tube may be positioned or affixed at least partially inside of the outer tube. The perforations on the inner tube may be located towards the second end when relative to the perforations on the outer tube, such that the perforations of the two tubes do not overlap. In other cases, the inner tube and the outer tube may positioned relative to each other such that the perforations of each tube partially or fully overlap.

In some aspects, the outer vapor collector forms a saddle having an outside diameter that is larger than the outside diameter of the outer vapor collector. In some cases, the outer vapor collector has a length selected based on an intended insertion length. In yet some cases, outer vapor collector has a length extending from the saddle selected based on an intended insertion length.

In some aspects, the sampling device may also include a hollow collection tube connector coupled to at least one of the outer vapor collector or the inner vapor collector proximate to the first end of the outer vapor collector or the inner vapor collector. In some cases, the hollow collection tube connector has an outside diameter selected to accommodate a vacuum collection tube to be attached to a measuring device.

In some examples, the perforations of the outer vapor collector have at least one of various sizes or shapes. In some cases, at least one of the size or the shape of the perforations of the outer vapor collector may be selected based on an intended use of the device. In some cases, the perforations of the inner vapor collector are smaller in size relative to the perforations of the outer vapor collector.

In some cases, the outer vapor collector may be designed to form a handle. In some examples, the outer vapor collector and the inner vapor collector may be made of a least one of: PFA, PEEK, PTFE, or passivated stainless steel.

BRIEF DESCRIPTION OF THE DRAWINGS

Preferred and alternative embodiments of the present disclosure are described in detail below with reference to the following drawings.

DETAILED DESCRIPTION

Figure 1:
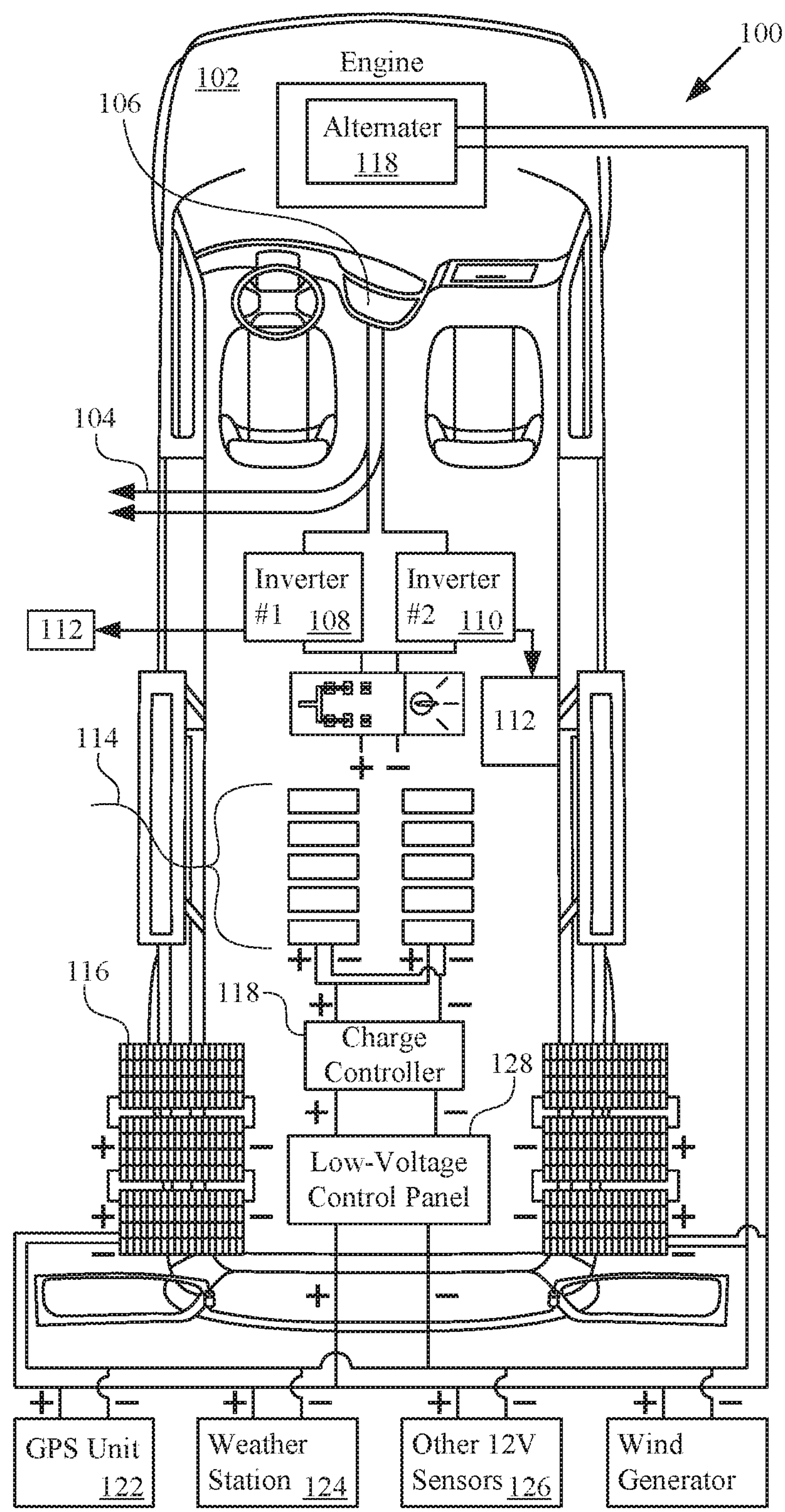
FIG. 1 illustrates an example of a mobile scientific platform implemented in a vehicle.

The present disclosure describes one or more embodiments of a mobile scientific platform, an auxiliary heat exchange system, and a vapor or sample collector, all of which may be used independently or combined in various different ways to address one or more of the problems with prior systems. It is to be understood that the use of absolute terms, such as "must," "will," and the like, as well as specific quantities, is to be construed as being applicable to one or more of such embodiments, but not necessarily to all such embodiments. As such, embodiments of the described systems, devices, and methods may omit, or include a modification of, one or more features or functionalities described in the context of such absolute terms.

Embodiments of the present disclosure may be operational with numerous general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Embodiments of the present disclosure may be described in the general context of computer-executable instructions, such as program modules, being executed by a computer and/or by computer-readable media on which such instructions or modules can be stored. Generally, program modules include routines, programs, objects, components, data structures, etc., that perform particular tasks or implement particular abstract data types. The present disclosure may also be practiced in distributed computing environments where tasks are performed by remote processing devices that are linked through a communications network. In a distributed computing environment, program modules may be located in both local and remote computer storage media including memory storage devices.

Embodiments of the present disclosure may include or be implemented in a variety of computer readable media. Computer readable media can be any available media that can be accessed by a computer and includes both volatile and nonvolatile media, removable and non-removable media. By way of example, and not limitation, computer readable media may comprise computer storage media and communication media. Computer storage media include volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

According to one or more embodiments, the combination of software or computer-executable instructions with a computer-readable medium results in the creation of a machine or apparatus. Similarly, the execution of software or computer-executable instructions by a processing device results in the creation of a machine or apparatus, which may be distinguishable from the processing device, itself, according to an embodiment.

Correspondingly, it is to be understood that a computer-readable medium is transformed by storing software or computer-executable instructions thereon. Likewise, a processing device is transformed in the course of executing software or computer-executable instructions. Additionally, it is to be understood that a first set of data input to a processing device during, or otherwise in association with, the execution of software or computer-executable instructions by the processing device is transformed into a second set of data as a consequence of such execution. This second data set may subsequently be stored, displayed, consequence of, or otherwise involve, the physical alteration of portions of a computer-readable medium. Such transformation, alluded to in each of the above examples, may also be a consequence of, or otherwise involve, the physical alteration of, for example, the states of registers and/or counters associated with a processing device during execution of software or computer-executable instructions by the processing device.

As used herein, a process that is performed "automatically" may mean that the process is performed as a result of machine-executed instructions and does not, other than the establishment of user preferences, require manual effort.

Mobile Scientific Platform

Referring to FIGS. 1-4, various implementations of a mobile scientific platform (which may be referred to either as "SciArk" or "SciLab") is illustrated. SciArk refers to a mobile scientific platform implemented in a vehicle, while SciLab refers to a mobile scientific platform implemented in a trailer, vehicle, or container that does not include a means of propulsion. In some aspects, the described mobile scientific platform may include systems and/or devices, which perform processes or methods, for measuring atomic elements and volatile organic (and inorganic) chemicals (VOCs) in air, liquids, and solids. In one specific example, the described mobile scientific platform may be an alternate-fuel, EPA Certified, field deployable, zero emissions, solar and wind assisted mobile scientific platform for measuring atomic elements and volatile organic (and inorganic) chemicals in air, liquids, and solids.

The described mobile scientific platform has applications in various areas, including for example the general fields of medical, pharmaceutical, environmental, energy, aerospace, drug enforcement, automotive, explosive detection, geological, mining/mineral/gas/oil exploration, forensic, agricultural, scientific, research, and veterinary applications.

Commercial applications for the described mobile scientific or measuring platform include, but are not limited to a mobile scientific platform for: environmental testing, radiological monitoring, mobile medical laboratories, rapid medical screening for viral, bacterial, and prion infections in plants, animals, and humans, heavy metal exposures in humans, human trafficking deterrence, fragrance and food industry, physiological health determinations, metabolic disorders, cancer detection, drug detection and efficacy studies, analytic lab procedures, soil contamination, geological surveys, atmospheric testing, soil measurements, environmental air sampling, air quality measuring, and explosives identification. Uses further include research facilities, mobile laboratories, doctor's offices, hospitals, veterinary clinics, outpatient facilities, surgical centers, blood banks, clinical laboratories, medical and veterinary schools, public health departments, morgues, as well as for agencies, such as, for example, WHO, EPA, NOAA, NASA, CDC, and NIH, FEMA, TSA, NTSB, DoD, FBI, ICE, DOJ, SWAT Teams, Bomb Squads, CIA, NSA, DHS, DEA, Fire and Police Departments, and state/local environmental/public health agencies. Suitable uses include wherever and whenever an uncontaminated source of uncondensed air (by removing condensation using, for example the AHE and AMVC devices, which are discussed below) is required for testing, monitoring, diagnosis, analysis, or evaluation of volatile organic (or inorganic) chemicals and atomic species in air, liquids, or solids.

The described mobile scientific platform enables analytic laboratories and scientific research to be mobile, field deployable, and portable, using integrated power systems in providing minimal to no environmental pollution, such as by utilizing alternative fuel options. The use of alternative fuel options may help to ensure robust, repeatable, and verifiable measuring samples without environmental contamination or extraneous data collection of VOCs or inorganics. In addition, the described mobile scientific platform may permit extended operating times for significant periods of time (such as days, for example), unattended by personnel.

Previous platforms have been piecemeal, "Frankenstein" units with no integration of redundant power systems, let alone alternative fuel options, or uncontaminated air samples. These previous platforms have been plagued by condensates in unheated sampling lines, not only compromising the data collected, but polluting the sampling line, and by introducing condensates in to the mass spectrometer or other scientific equipment used. For these reasons, an Auxiliary Heat Exchanger (AHE), as described more fully below, when used, for example with the described mobile scientific platform, may overcomes one or more of these issues. Additionally, previous mobile scientific platforms have used conventional fossil fuels, like gasoline and diesel, which further and dramatically complicates data collection and analysis. Combustion products from burning these fossil fuels in proximity to and collected in the sampling line and other scientific equipment contaminate the data collected. In addition, previous platforms have required constant operation, sample collection, and data interpretations by scientists with PhDs, on site. The described mobile scientific platform may, in some cases, additionally address one or more of these issues with prior systems, by utilizing alternative fuels and/or utilize longer term power storage for longer unattended use.

As noted, in some aspects, the described mobile scientific platform is an alternative-fuel vehicle. The platform, in one aspect, can be integrated into a vehicle that runs on gasoline. In some cases, the vehicle can be modified to that it can also run on propane or compressed natural gas (CNG), or other source. In one example, the described mobile scientific platform can be manually switched in the driver's compartment to run on different fuels. Gasoline is the "dirtiest" of fuels, producing hundreds of combustion by-products, but it has the highest energy content per unit of fuel. Diesel is less "dirty," but it produces black particulates, which can clog and pollute air sampling devices. It too has a high-energy content per unit of fuel, but less so than gasoline. Propane is much cleaner and produces very few particulates. Its energy content per unit of fuel is less than diesel or gasoline. CNG is the cleanest of the fossil fuels, producing the least particulates, but its energy content per unit volume is the least of all the fossil fuels. In some examples, one or more detectors may be implemented to detect when, for example, measuring equipment is activated or powered on, and/or when samples are being collected. Upon such detection, the vehicle may be automatically switched or converted from operating on gasoline, diesel, or other "dirty" fuel, to a cleaner energy source, such as propane, CNG, or other sources.

In another aspect, the mobile scientific platform can be integrated into an electric vehicle. For example, an all-electric vehicle with a duplicate set of batteries to run the scientific equipment in the vehicle could be used. In this instance, the auxiliary batteries could be charged using brake energy, alternator, solar panels, and wind turbines.

The described mobile scientific platform preferably runs on gasoline, propane, CNG, or electric. The described mobile scientific platform may, in some cases, be a zero emissions platform.

FIG. 1 illustrates an example of a mobile scientific platform 100, integrated into a vehicle 102. It should be appreciated that vehicle 102 may take any of a variety of forms, including a utility vehicle, truck (standard pick-up truck, flatbed truck, or commercial trucks, such as semi-trucks, etc.), van (such as a Ford Transit or other similar van), car, etc., and have any of a variety of features described herein. As described above, vehicle 102 may utilize any of a number of propulsion mechanisms, such as running on gasoline, propane, CNG, or electric, or a combination thereof.

In some cases, platform 100 can be connected to traditional shore power (120 or 240 volts, for example), through male receptacles or plugs 104 (e.g., 2 120 V/30 A receptacles) located on the side of the vehicle, to provide the energy requirements of the scientific equipment inside the vehicle 102. Preferably, the shore power is routed to a UL approved industrial control panel 106 with breakers for circuit protection. One or more robust pure sine wave inverters 108, 110 may be connected to the control panel 106. Scientific equipment 112 (e.g., measuring device), like mass spectrometers and gas chromatographic equipment (or any other measuring equipment, for example, that may require 120 V/20 A power), may be plugged-in to the sine wave inverters 108, 110, either internal to the vehicle 102 or outside the vehicle 102. Pure sine wave power is preferable to prevent damage to sensitive scientific instrumentation and micro-circuitry. In addition, as an alternative source of power, batteries 114, such as, for example, pure lead AGM deep cycle 12 volt batteries are arranged in series (or an array of 6 volt batteries connected in series and parallel, or a configuration of 24 volt and 48 volt batteries can also be used) and connected to the sine wave inverters 108, 110, thus providing constant power for the scientific equipment 112 when shore power is unavailable. In some aspects 10 more AGM batteries may be used. Additionally or alternatively, the use of various types of batteries can be substituted for the AGM batteries 114, like lithium-ion batteries, a nickel-manganese-cobalt oxide cathode grid battery (called an NMC battery), or nickel-cobalt-alluminum batteries, or nickel cadmium batteries, or any batteries with enhanced performance through the introduction of silicon in to the graphite anode, or any of high performance batteries with enhanced watt capacity and/or high amp hour ratings, arranged in series, parallel, and/or connected in both series and parallel, together, including solid state batteries. In some aspects, each battery may be connected to breakers to enabling hot swapping of batteries as need arises.

In some cases, the described mobile scientific platform 100 can be configured to run for a minimum of 12 hours without shore (e.g., any external) power, but may run for longer or shorter periods of time depending on the number and type of batteries used, as well as the electrical demands of analytic equipment in the mobile platform. A power source that can run for 12 hours may permit the scientific equipment 112 to run continuously between job-sites without the need to power down the scientific equipment, which sometimes takes in excess of 4 hours on initial start-up, not including time to calibrate the equipment. In one specific example, a battery bank of ten (10) six (6) volt batteries arranged in series and in parallel may be used to provide 12-volt power to the inverters. Each battery may be 400 amp/hours, providing up to 12 or more hours of continuous power for most scientific instruments.

In some examples, AGM battery charge is maintained by one or more of multiple integrated systems. The charge may be augmented by one or more solar panels 116 mounted on the top of the vehicle 102. The solar panel(s) 116 may include a 480 or 680 Watt, four-panel array (with a charge controller 118) connected directly to the battery array 114. Additional portable solar panels (with charge controllers 118) can be carried in the vehicle and positioned outside to provide additional charge to the batteries 114. In one specific example, 6 monocrystalline solar panels, totaling 680 watts (29.5 amp/hour), may be used with charge controllers. Additional stand-alone solar panels can be daisy-chained to the existing panels, which may be permanently installed on the roof and/or the side of the mobile scientific platform. Additionally or alternatively, a heavy duty alternator 118 may be installed in the vehicle 102 (with a charge controller) and connected to the AGM batteries 114 for additional charge whenever the vehicle is running.

With reference to yet a further embodiment, a vertical wind turbine (not shown) may be mounted on the vehicle 102 to charge the batteries 114 to the inverters 108, 110 when the mobile platform 100 is stationary. A RAM air turbine (RAT) (not shown), as is used in aircraft to provide back-up power to mission critical flight systems when power is lost, may additionally or alternatively be mounted to the vehicle 102 for charging the batteries 114 when the platform is mobile.

Figure 2:
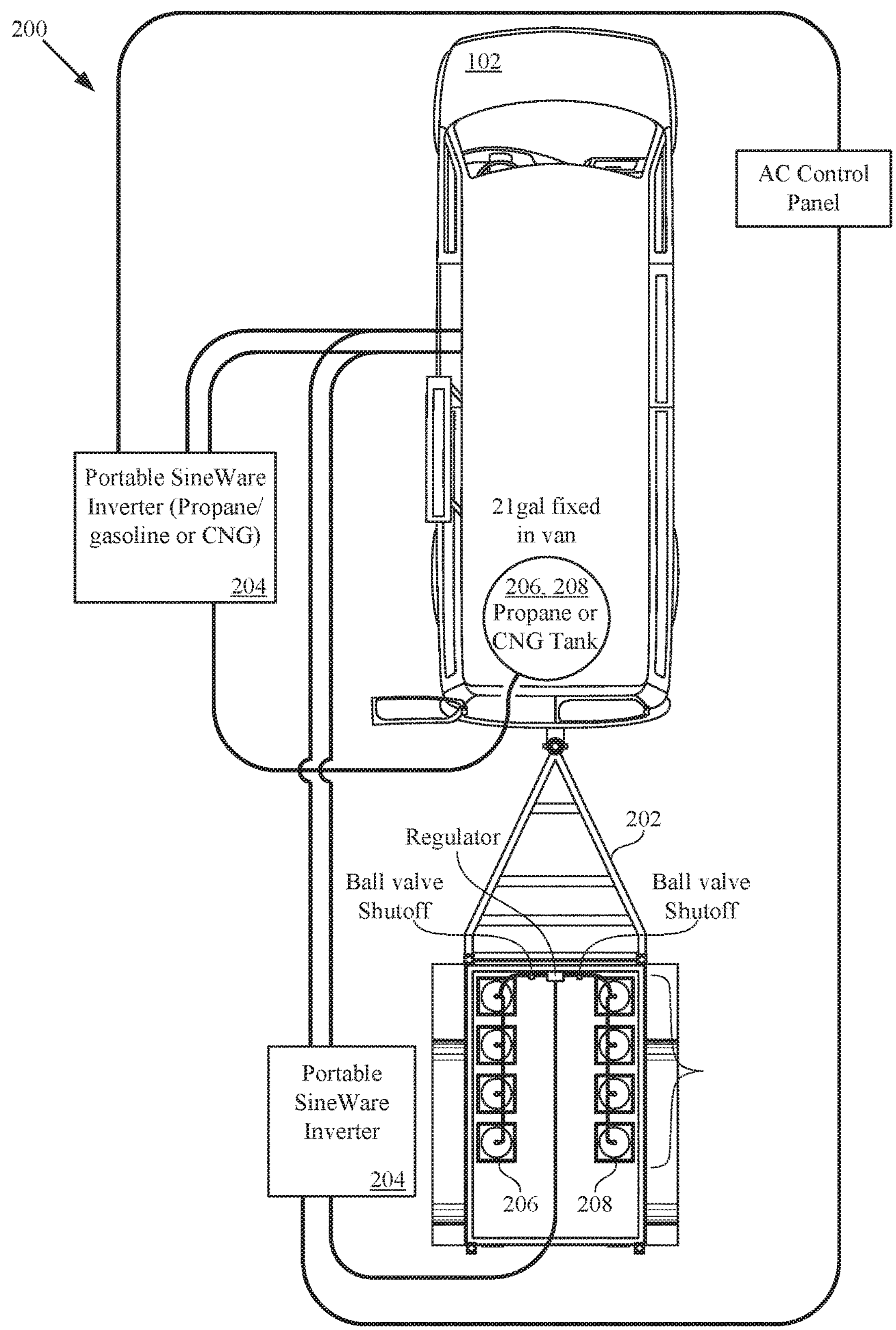
FIG. 2 illustrates an example of a mobile scientific platform implemented in a vehicle and trailer.

With reference to FIG. 2, another implementation of a mobile scientific platform, 200 is illustrated. Platform 200 may include a vehicle, such as vehicle 102, and a trailer or component 202 external to vehicle 102. In some aspects, a portable sine wave inverter 204 (e.g., producing 4500 Watts), which has been converted to run on gasoline/propane/CNG, may also be used to provide shore power whenever energy requirements dictate. The portable inverter 204 can be conveyed inside the vehicle 102, or contained in a towed trailer 202, which may also have a supply of propane or CNG tanks 206, 208. The portable inverter 204 can run off propane/CNG tanks 206, 208 permanently installed in the alt-fuel of the mobile platform, either in a vehicle 102 or trailer 202 or other compartment or container, such that the portable inverter 204 can run off the tanks in the towed trailer/container. Pure sine wave electricity generated by the portable inverter 204 is transmitted to the shore power ports on the mobile platform.

In some aspects, whenever the voltage in the battery bank reaches 11.0 VDC, a sensor from the mobile scientific platform may connect to the portable inverter (e.g., located 25 feet from the van), which may start its engine automatically. Once engaged, the portable inverter provides "shore power" to the mobile scientific platform. The run-time of the portable inverter can be manually or automatically adjusted and regulated (e.g., via timers, controllers, etc.). The portable inverter can be cargo-carried on the back of the mobile scientific platform or it can be towed in a small trailer, which also has a fuel supply of DOT approved propane tanks.

The described mobile scientific platform 100, 200 may provide an unlimited and versatile system of integrated power support. It permits the extended and unattended running of measuring equipment in the stationary mode for pure air sampling. In mobile operation, the propulsion of the vehicle 102 using propane/CNG permits "clean" air sampling. Sampling is preferably performed by a sampling device, such as one or more sample collectors or Atomic/Molecular Vapor Collectors (AMVCs), discussed more fully below. Gasoline propulsion may be used convey the vehicle 102 to and from job sites when air sampling is not in operation.

Referring back to FIG. 1, according to one embodiment, attached to the top of and/or inside of the vehicle 102 are an array of 12 volt devices 122, 124, 126, all connected to a low voltage control panel 128. On the top of the vehicle may be attached a GPS locator 122 and a weather station 124, which measures, temperature, wind speed, wind direction, humidity, pressure, dew point, and the like, and a wind turbine. Inside the vehicle 102 may be various 12 volt devices or sensors (not shown). Depending on the VOCs or inorganics under investigation, the vehicle 102 can be outfitted with radiological, ammonia, CO2, methane, and nitrogen sensors, to name but a few. All or some of a variety of 12 volt auxiliary sensors, as well as data from the scientific instrumentation inside the van (such as mass spectrometers, gas or liquid chromatometers) may be integrated with a server or laptop for display, interpretation, and/or analysis. The data obtained from any of these sensors can be stored for future use, used to trigger automated alert systems, or transmitted through Bluetooth or Wi-Fi hot spots for real-time analysis in remote laboratories or client centers. In some aspects, the data obtained from the one or more sensors may be uploaded and made accessible via one or more servers, such as via log-in credentials.

Figure 3:
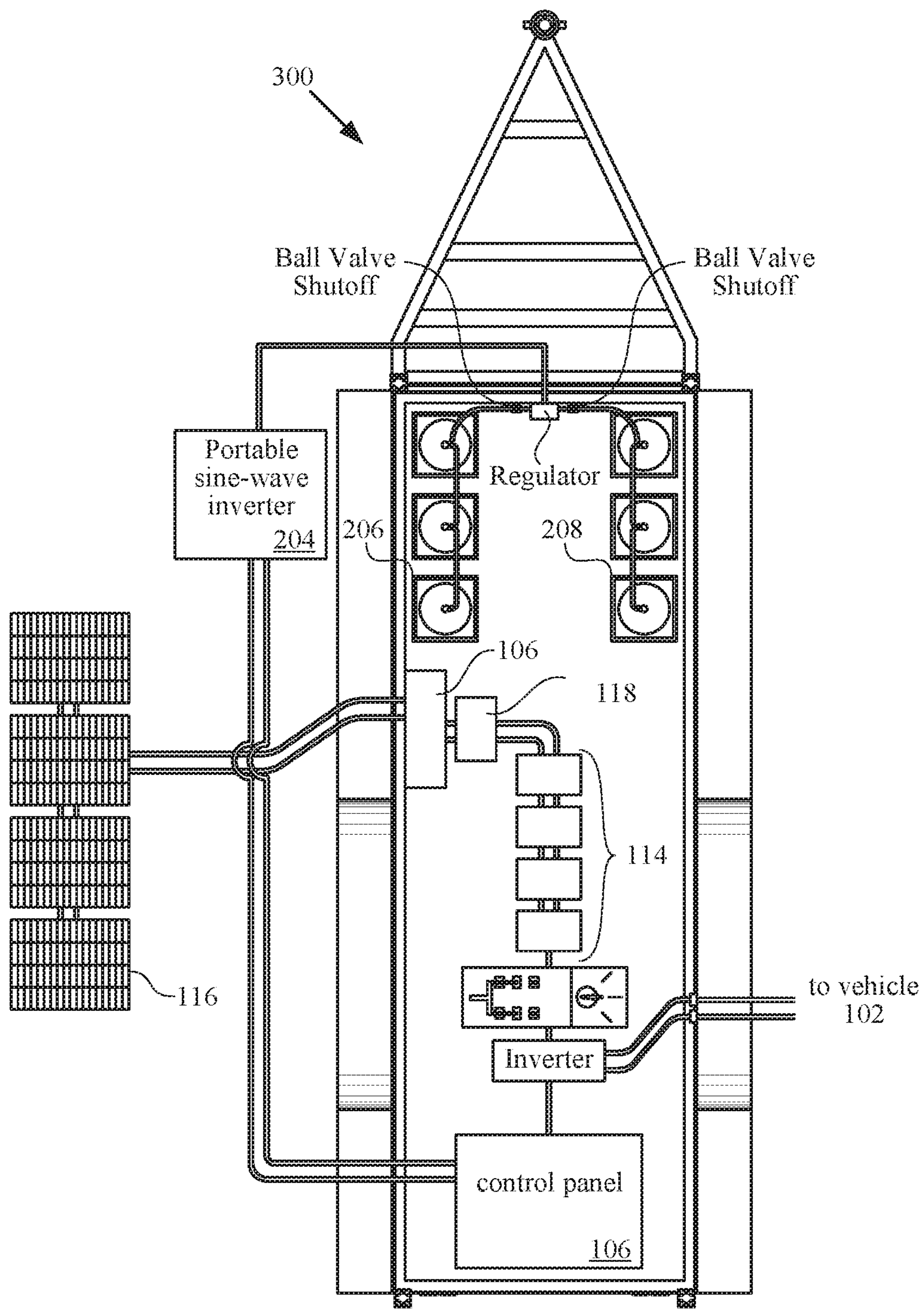
FIGS. 3 and 4 illustrate examples of a mobile scientific platform implemented in a trailer or other container.

In another aspect, as illustrated in FIG. 3, power generation equipment, such as control panel 106, batteries 114, solar panel(s) 116, charge controller 118, propane or CNG tank(s) 206, 208, may be housed in a trailer, such as trailer 300. Trailer 300 may be towed behind and connected to measuring equipment (e.g., housed in a vehicle, such as vehicle 102) via one or more portable inverter(s) 204.

Figure 4:
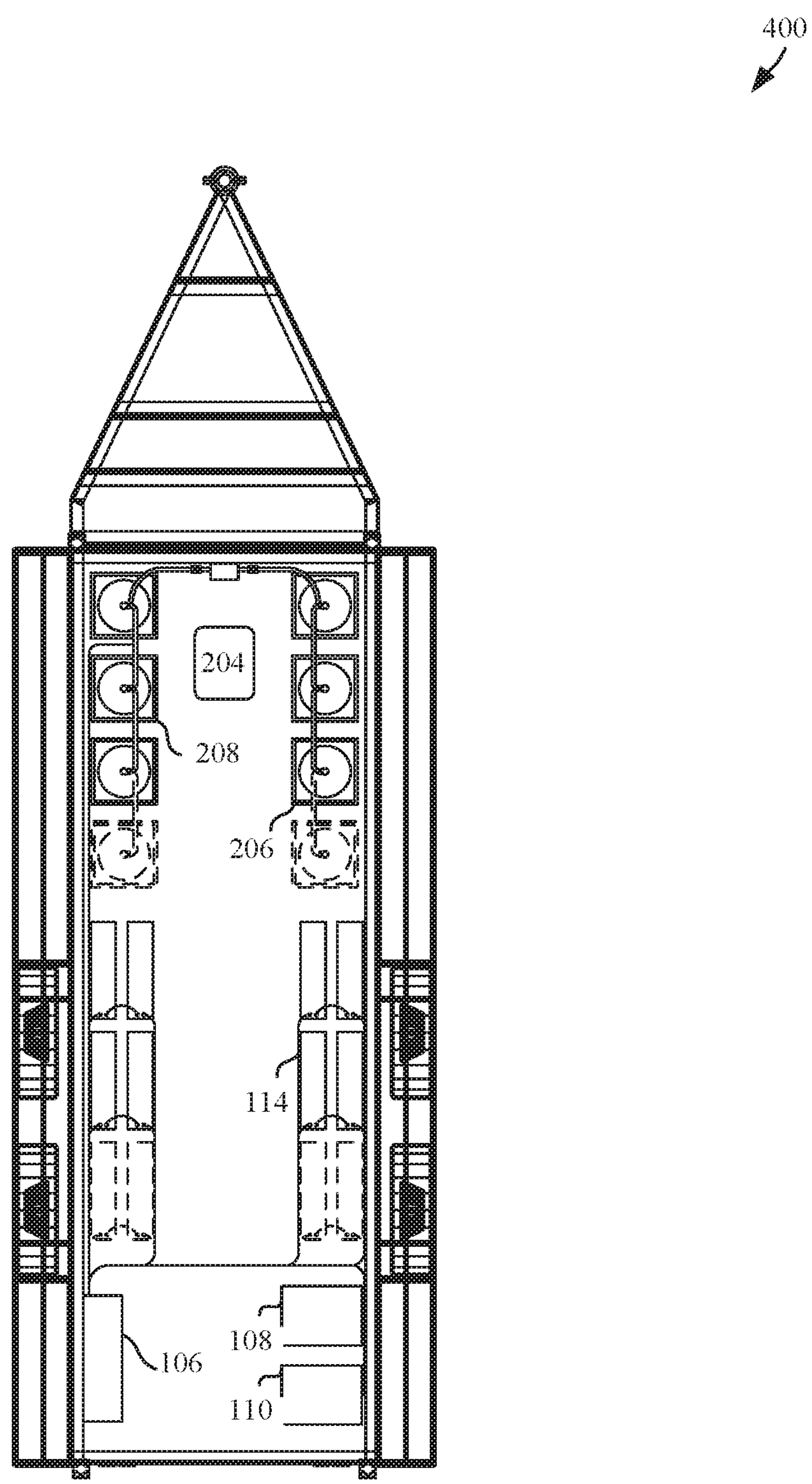

In one aspect, a portable trailer 400, as illustrated in FIG. 4, could be outfitted with propane/CNG tanks 206, 208, an UL Industrial Control Panel 106, a pure sine wave inverter or inverters 108, 110, solar panels 116, optional sensors (weather station, GPS, CO2, etc.) 122, 124, 126, a wind turbine (not shown), and an AGM battery array 114 in series and/or parallel, essentially duplicating platform 100, but without a primary propulsion system (i.e., an engine). The scientific equipment used for analysis in this embodiment could be housed inside buildings located close by, but still powered from the portable trailer 400, or included in the trailer 400 itself, or in a vehicle that tows or is located proximate to trailer 400. In some aspects, trailer 400 may have a larger surface area than vehicle 102, such that additional monocrystalline solar panels or wind turbines may be temporarily or permanently placed on the trailer 400 to keep the batteries to the inverters at full charge. Upsizing of the trailer 400 may allow additional scientific instrumentation to be installed and operated within trailer 400.

It should be appreciated that the above implementations of the described mobile scientific platform are only given by way of example. Other implementations, such as adding or removing features from one implementation to another implementation, removing some features from an implementation, or changing the location of one or more features, such as from the vehicle to the trailer and vice versa, are contemplated herein. A number of other components or features, such as features necessary for the operation/safe operation, of the vehicle and/or trailer are contemplated herein, but for the sake of conciseness, are not specifically described herein.

As discussed herein, features of the mobile scientific platform may include, for example: an automotive, truck or truck-like vehicle; integrated power support; mobile scientific laboratory platform; alt-fuel options; extended range and unattended use; no pollution contamination in static mode; negligible contamination when in mobile operation; and may provide real time results. In some aspects, the mobile platform may also benefit from the use of an auxiliary heat exchanger (AHE) device or system for eliminating condensate contamination of air samples, and/or one or more atomic/molecular vapor collectors (AMVC) attached to the AHE, as described in greater detail below.

It should be appreciated that any type of mass spectrometer (or other scientific, or spectrographic devices) can be used with mobile scientific platform depending on the VOCs, atomic elements, or inorganics under investigation. Mass spectrometers are known and are therefore not discussed in detail herein. For example, a MALDI MS for large organic molecules might be used to detect cancers, Zika, etc., whereas a PTRMS might be used for drug/pharmaceutical/veterinary applications. Another example includes DART instrumentation, which is an atmospheric pressure ion source that instantaneously ionizes gases, liquids and solids in open air under ambient conditions for uses in the fragrance industry, pharmaceutical industry, foods and spices, forensic science and health.

One specific example of a unique application for the mobile scientific platform includes the use of PTRMS technology. PTRMS, like the TOF 6000 from Ionicon, can identify (real time) volatile organic chemicals (VOCs) with extreme precision, i.e., parts per quadrillion. The use of this instrumentation may prove useful in the detection of explosives, drugs, and human trafficking, as well as in the nascent field of breath research, among other examples. Installed in the described mobile scientific, PTRMS may be mobile, rather than confined to a brick and mortar analytic lab, or an academic research laboratory. Moreover, the mass spectrometer has a continuous clean power supply, so there is no need to power-cycle the instrument, which can take 4 hours, or more; the instrument is always "on." Additionally, in the zero emissions (either moving or stationary in different examples) mode, the described mobile scientific platform may not contribute any VOCs which might contaminate air samples. In mobile operation, the mobile scientific platform may contribute negligible hydrocarbon emissions when running on propane or CNG, perfect for sampling VOCs over distances. For these reasons, the use of PTRMS in the mobile scientific platform opens new vistas of research, as it does for other equipment manufacturers and researchers.

Figure 5:
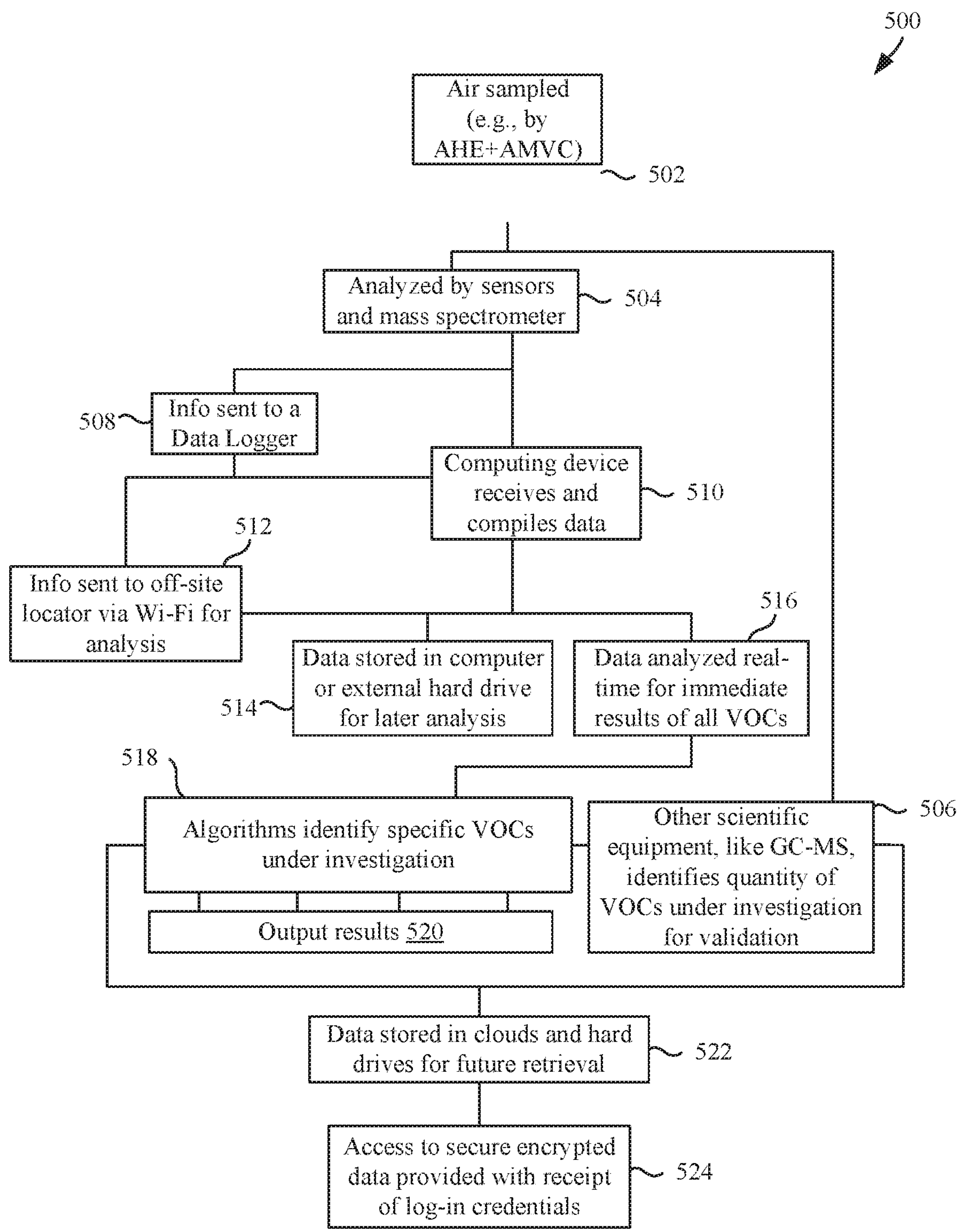
FIGS. 5-7 illustrate various example processes that may be performed by or in conjunction with a mobile scientific platform, as illustrated in FIGS. 1-4.
Figure 6:
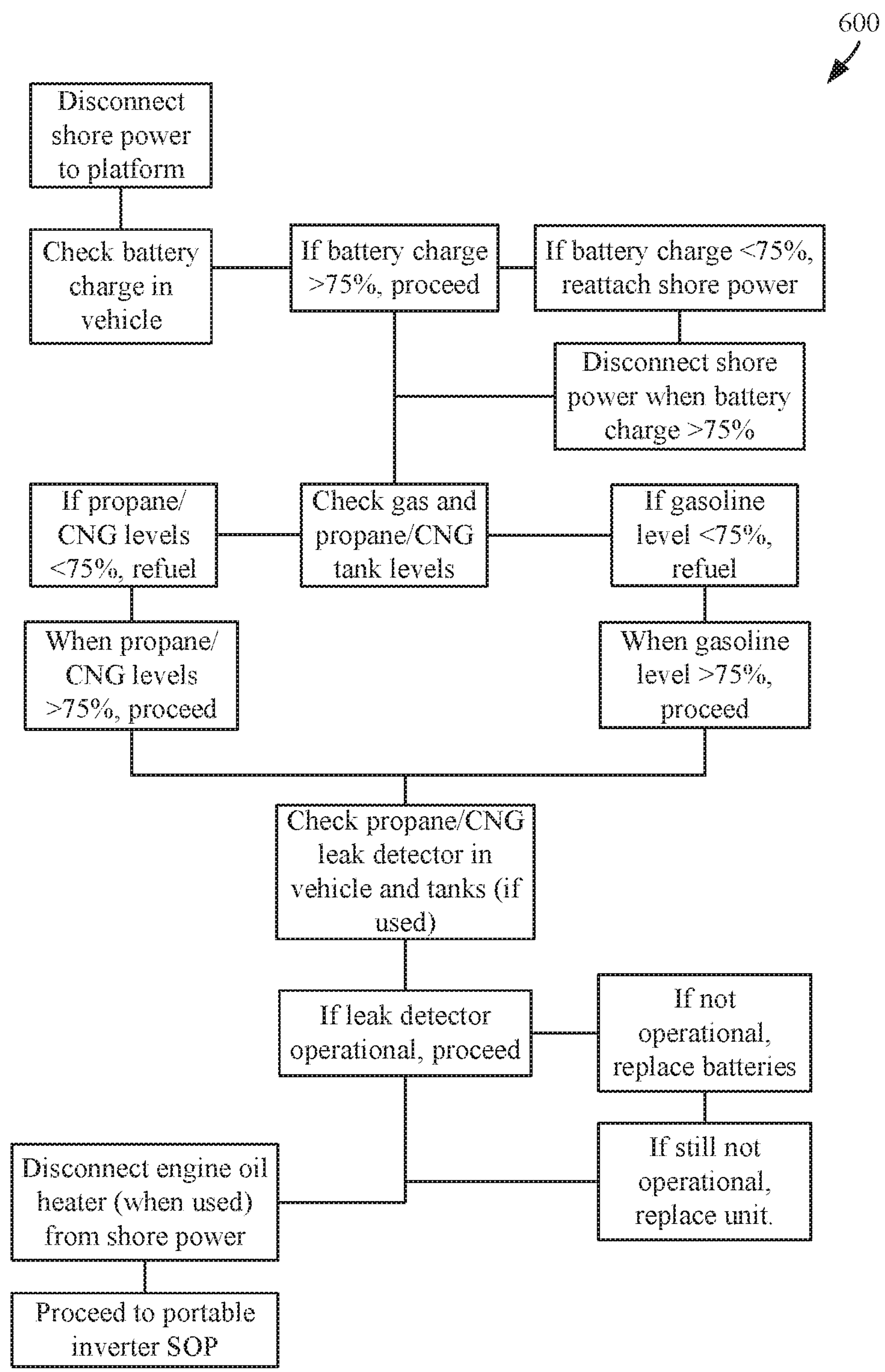
Figure 7:
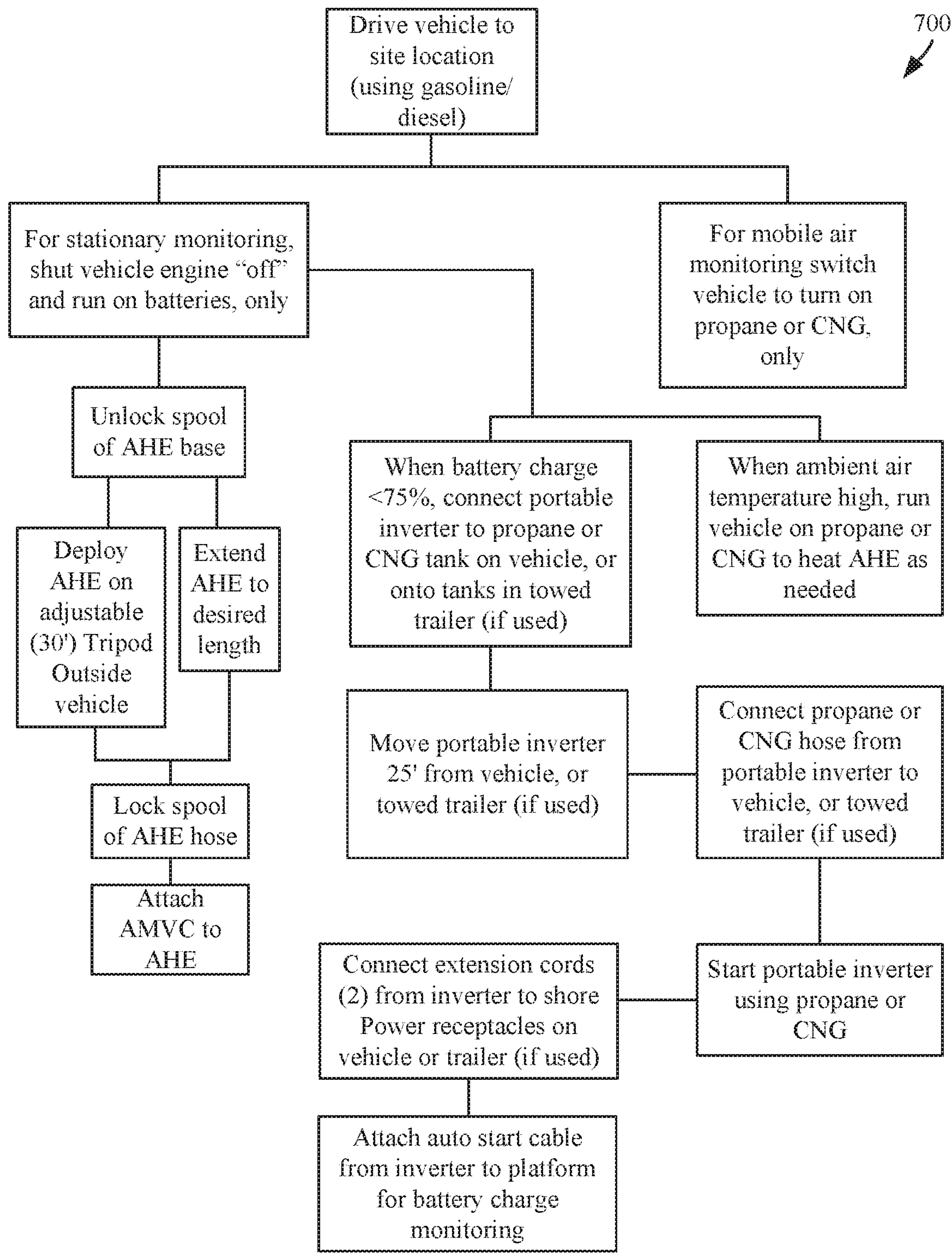

FIGS. 5-7 illustrate various aspects of the operation of the mobile scientific platform.

FIG. 5 illustrates an example process 500 for analyzing data collected by one or more sensors of the mobile scientific platform. Process 500 may be performed in whole, part, or in conjunction with any variations of the mobile scientific platform described above. Process 500 is only given by way of example, such that certain operations may be substituted for others, or not performed.

As illustrated, process 500 may begin at operation 502, where air or gas is sampled, for example, using an auxiliary heat exchange system and/or an atomic/molecular vapor collector, as descried in further detail below. The sampled air or gas may then be analyzed by sensors, one or more mass spectrometers, or other scientific equipment such as a Gas Chromatography (GC), or Gas Chromatography Mass Spectrometer (GC-MS), at operations 504 and 506. Following operation 504, the sensor/mass spectrometer results or data may be optionally sent to a data logger at operation 508, and in turn sent to a local computing device at operation 510 or sent offsite via at operation 512 any of a variety of communication links (LTE, Wi-Fi, other WLAN technologies, and so on). In the case that the data is sent to a computing device, the data may then be sent off site (for example after a local record of the data is saved on the local computing device) at operation 512, and/or may be stored locally at operation 514, and/or may be analyzed at operation 516 in real-time or near real-time. If the data is analyzed at operation 516, then process 500 may proceed to operation 518, where algorithms may be used to identify specific VOCs, atomic elements, or inorganics under investigation, which may produces results that may be output at operation 520, such as by being visually displayed on the local computing device (and typically stored in memory of the computing device). In some aspects, when other scientific equipment is used to analyses the samples at operation 506, the results or data output by the equipment may be analyzed to identify VCOs, at operation 518. The results or output data from operations 518 and in some cases, 506, may then be stored in a central location at operation 522, such as via a cloud based service, private servers, etc., and accessed at operation 524, for example, via secure log-in credentials, via techniques and system well known in the art.

FIG. 6 illustrates an example process 600 for verifying a power source used for the mobile scientific platform is operational.

FIG. 7 illustrates an example process 700 for operation of a mobile scientific platform.

Auxiliary Heat Exchanger

Turning to FIGS. 8-15, an auxiliary heat exchanger (AHE), is illustrated. The described auxiliary heat exchanger has applications is the general fields of environmental, energy, medical, pharmaceutical, forensic, drug enforcement, explosive detection, food, automotive, energy, scientific, and veterinary applications.

The described auxiliary heat exchanger may include a system for eliminating the contamination of condensates in air (or any gas or combination thereof) sampling collection tubes and scientific measuring equipment. The described auxiliary heat exchange system uses heat exchange from pressurized closed liquid coolant systems in internal combustion engines (e.g., gasoline, diesel, steam, natural gas, hydrogen, or propane) as well as any electrical engines in which waste heat is generated. In some aspects, the described auxiliary heat exchanger may be passive, continuous, and the heating liquid or gas may flow in the same or opposite direction as samples collected.

Figure 8:
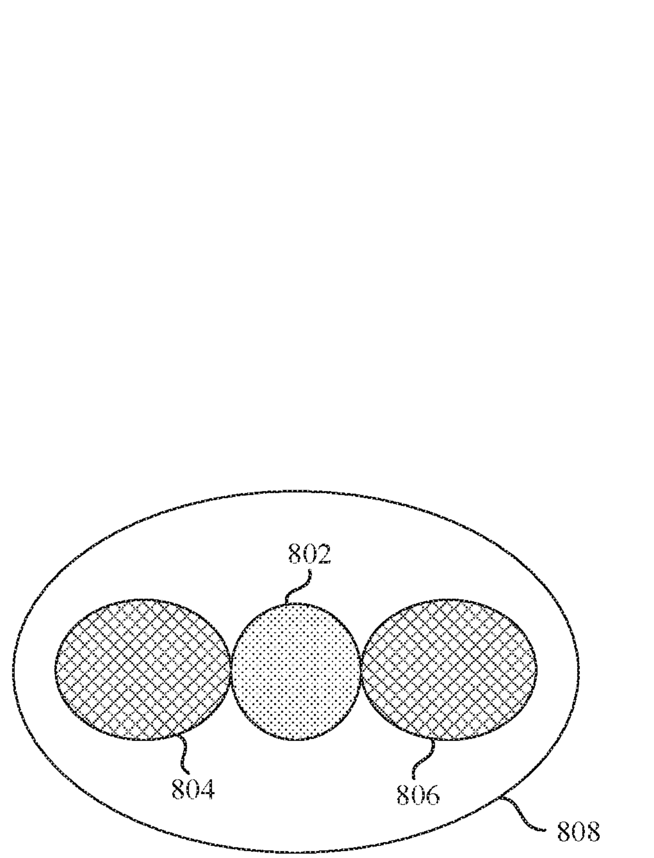
FIG. 8 illustrates an example supply line that may be implemented as part of an auxiliary heat exchange system.

According to one embodiment, a secondary supplemental (auxiliary) closed pressurized heat exchange hose is employed to passively heat air inside of an inserted inlet tube, also called a tracer tube, or a sample line, used for air or gas sampling to eliminate loss of analyte due to condensation. As illustrated in FIG. 8, the auxiliary heat exchanger may utilize a cable, hose bundle, or supply line 800 that includes a sample tube 802 and one or more adjacent tubes 804 (a first conduit), 806 (a second conduit), for carrying liquid that is warm or hot (or any temperature that is higher than the temperature of the sampled gas, and can also stay at a temperature that is higher than the sampled gas over the entire or substantially the entire duration of the supply line). Cable or supply line 800 may be connected to any source of hot liquid, or even gas. One example includes connecting the supply line 800 to a heating/cooling system of a combustion engine.

One specific implementation example of a supply line or bundled hose is described below. It should be appreciated that the following is only given by way of example, and that other implementations and design details are contemplated herein. In some aspects, the heavy steam traced bundled hose 800 contains two process tubes 804 (a first conduit), 806 (a second conduit) and one tracer (sampling) tube or conduit 802. Air samples are conveyed in the tracer tube or conduit 802. Liquid coolant (or gaseous or other substance coolant) is recirculated from the primary coolant system in the process tubes 804, 806. The process tubes 804, 806 may be made of Teflon (PFA), while the air sampling tube 802 may be made of Ultra High Purity Teflon (PFA), or similar non-reactive materials like PEEK or PTFE. In some cases, the processing tubes 804, 806 may be in direct contact with the tracer tube 802, thus facilitating maximum heat transfer to help maintain consistent higher process temperatures. In some aspects, all three tubes may be incased in water soluble chloride (preferably less than 100 ppm) in an absorption-resistant fibrous glass insulation that resists wicking. The insulation may be covered in a non-halogenated thermoplastic urethane, such as casing 808 (e.g., external casing).

Commercial applications for the described auxiliary heat exchanger include, but are not limited to: environmental testing, radiological monitoring, mobile laboratories (such as the described mobile scientific platform), rapid medical screening for viral, bacterial, and prion infections in plants, animals, and humans, heavy metal exposures, fragrance and food industries, human trafficking deterrence, physiological health determinations, metabolic disorders, cancer detection, drug detection and efficacy studies, analytic lab procedures, and explosives identification. Further uses include research facilities, mobile laboratories, doctor's offices, hospitals, veterinary clinics, outpatient facilities, surgical centers, blood banks, clinical laboratories, medical and veterinary schools, public health departments, morgues, as well as agencies such as, for example, FBI, ICE, DOJ, SWAT Teams, Bomb Squads, CIA, NSA, WHO, EPA, NOAA, NASA, CDC, and NIH, FEMA, DoD, DHS, DEA, NTSB, Fire and Police Departments, and state/local environmental/public health agencies and DEA. AHE is well suited to applications in which an uncontaminated source of uncondensed air was required for testing, monitoring, diagnosis, analysis, or evaluation.

The described auxiliary heat exchange system may be used to collect atomic and molecular vapors from air, liquid, or solid samples without the problems of and contamination from condensates in sample lines and scientific measurement equipment. Condensation typically occurs in air sampling lines whenever there is a drop in air temperature between the vapor source and the measurement at the instrument. Ambient air samples should be lower in temperature than the same measured sample in scientific equipment, like mass spectrometers. The air entering a mass spectrometer would preferably be higher than the ambient air sampled. Any drop in temperature below ambient, before reaching the mass spectrometer, for example, may result in loss of compounds of interest to the walls of the sampling system, or in the mass spectrometer, or similar measurement equipment, and may result in condensate contamination in the sampling line or in the mass spectrometer, or similar measurement equipment. Also, higher relative humidities and higher atmospheric pressures of air samples also contribute to condensation in the sampling line and in scientific measuring equipment. Besides the problems of air samples turning in to a liquid, the condensates are more easily absorbed as liquids onto and into the sampling line. These problems confound and contaminate true, reliable, and verifiable data collection measurements for researchers, and are addressed by the described auxiliary heat exchanger.

Prior approaches to air sampling have been plagued with non-constant temperatures or cold spots in the tracer tube, thus leading to condensation. The longer the tube, the more chance for condensate formations. Condensation contaminates the interior of the tracer tube, which causes artificially elevated background signals in the scientific equipment. These condensates must then be "baked out" of the sampling system, causing measurement downtime. Moreover, when condensates traveling in the tracer tube reach the scientific measuring equipment (like mass spectrometers) expensive decontamination, tracer tube replacement, and long equipment down times can result. The described auxiliary heat exchange system addresses one or more of these problems.

Figure 9:
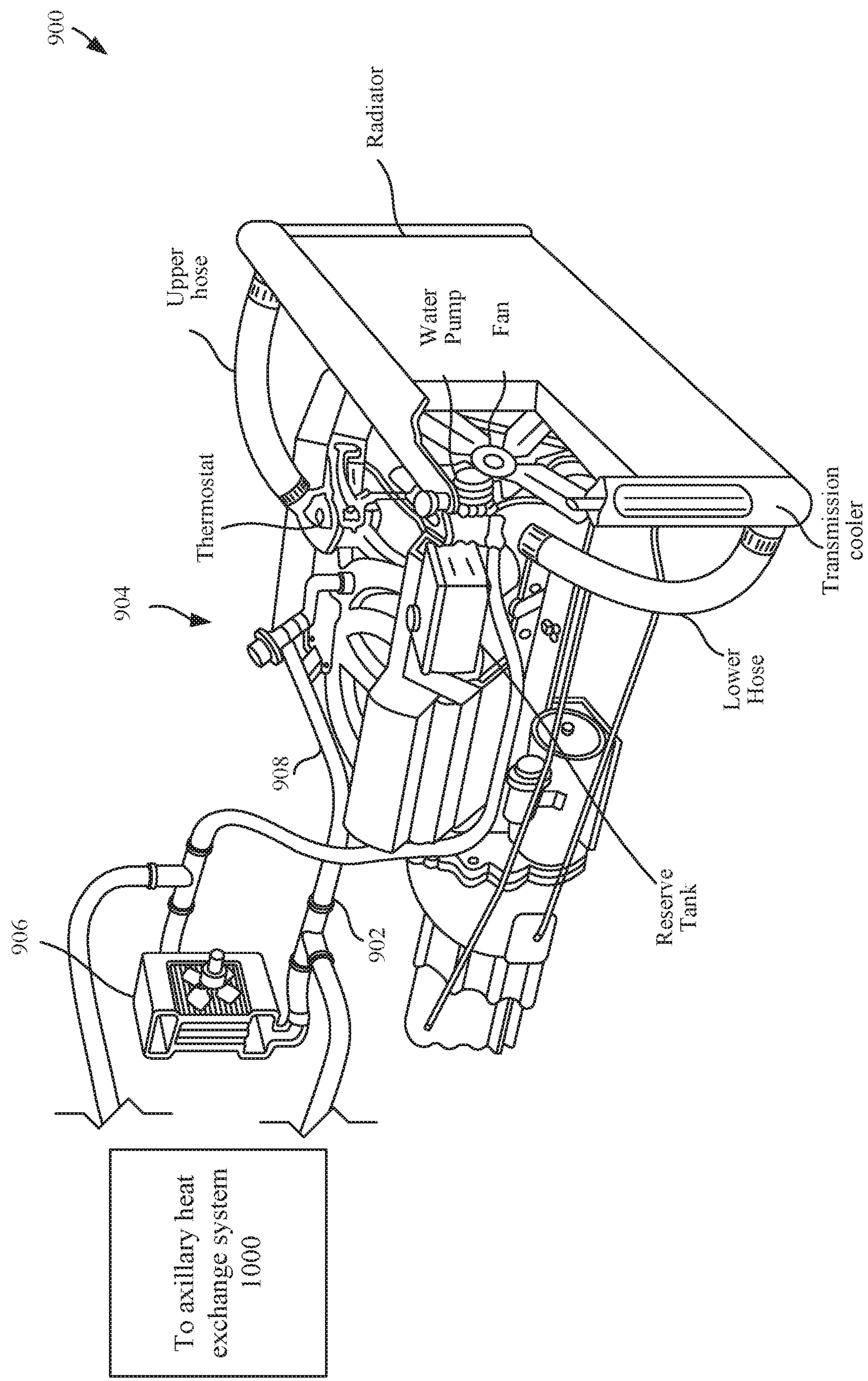
FIG. 9 illustrates an example cooling/heating system of a combustion engine to which an auxiliary heat exchange system may be coupled.

An example of a general closed pressurized system 900 of liquid cooling/heating for internal combustion engines is illustrated in FIG. 9. An upper heater hose 902 carries hot coolant from engine block 904 to heater core 906. The coolant is slightly cooled as a result of operation of the heater core 906, for example in the cab of the vehicle, and a lower heater hose 908 supplies cool coolant to engine block 904.

Figure 10:
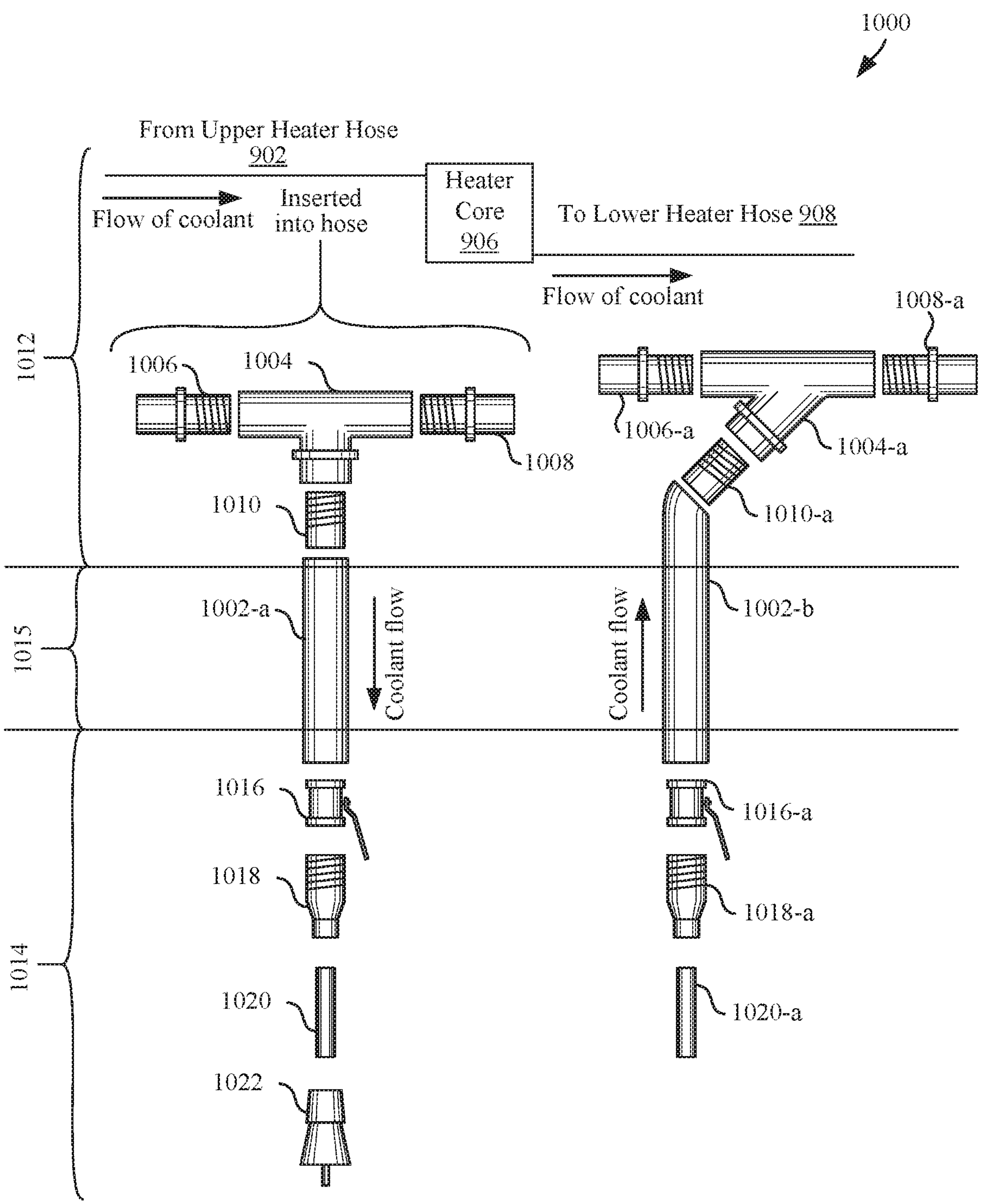
FIGS. 10 and 11 illustrate aspects of an example auxiliary heat exchange system.

In some aspects, when used in a mobile platform, such as the mobile scientific platform described above, the auxiliary heater exchanger may include a recirculating pressurized passive secondary closed heat transfer loop 1000, as illustrated in FIG. 10. The secondary closed heat transfer loop 1000 may be attached to the primary cooling system 900, typically used in internal combustion engines, such as may be part of the mobile scientific platform. The secondary closed heat transfer loop 1000 may be attached at the upper heater hose 902 and to the lower heater hose 908, as illustrated in FIG. 9. Hotter liquid coolant from the engine block 904 enters the cabin's heater core 906 through the upper heater hose 902. After passing in to the heater core 906, the liquid coolant is recycled back to the engine 904 through the lower heater hose 908 at a slightly lower temperature, especially when the heater is used in the passenger compartment. Attached to the heat transfer loop 1000 is a heavy steam-traced bundled hose 1002-*a*, such as the bundled hose illustrated and described in reference to FIG. 8, (containing two process tubes and a tracer tube). Coolant is recirculated in the process tubes, while the tracer tube, which is in direct contact with the process tubes, ensures constant or increasing temperatures from the air sampling source to the scientific equipment used, thus eliminating or greatly reducing condensation of the air sample.

According to one embodiment, as illustrated in FIGS. 9 and 10, the auxiliary heater exchanger can be connected to any closed pressurized recycled system of air or liquid heating/cooling systems used for internal combustion engines. The secondary (or auxiliary) closed heat transfer loop 1000, which may include the auxiliary heater exchanger, can be teed in to the hot portion of the radiator heater hose 902 using, for example, a T connector 1004 and/or two barbs (male) 1006, 1008, which may be threaded on at least one end to couple to the T connector 1004. The upper heater hose may be ¾ inch OD (typically between 80 to 100 degrees centigrade) under pressures of 4-30 PSI, as well as the T connector 1004 and barbs 1006, 1008 (the threads may be ⅜"). The T connector 1004 and/or barbs 1006, 1008 may be made of/interconnect with an insulated high temperature rubber or silicone hose, commonly found in automotive radiator hoses. In some examples, the tee 1004 is stepped down from a ¾ inch barbed fitting to a ⅜th inch barbed fitting and secured by hose clamps at all connections. From the ⅜ths inch barbed fitting 1010, a ⅜ths hose 1002-*a* is attached, running from the engine compartment 1012 to the cargo area 1014 (through driver compartment 1013) of the vehicle where scientific equipment is located. The hose 1002-*a* is also connected to a ⅜ths ball value shut-off 1016 for safety. Attached to the ball valve 1016 is a ⅜ths or ¼ inch compression fitting 1018 to connect a small piece of high purity Teflon (PFA) tubing 1020. The PFA tubing 1020 is connected to a male quick-disconnect 1022, which may be color-coded and lock code protected, so a green male quick-disconnect cannot be attached to a yellow female quick-disconnect, for example. As similar arrangement or configuration on the return flow (e.g., including similar numbered components 1022-*a* (not shown), 1020-*a*, 1018-*a*, 1016-*a*, 1002-*b*, 1010-*a*, 1008-*a*, 1006-*a*, 1004-*a*) may connect the coolant line back to the lower heater hose 908. The return flow may include different color and lock codes, to ensure the lines are kept separate.

Figure 11:
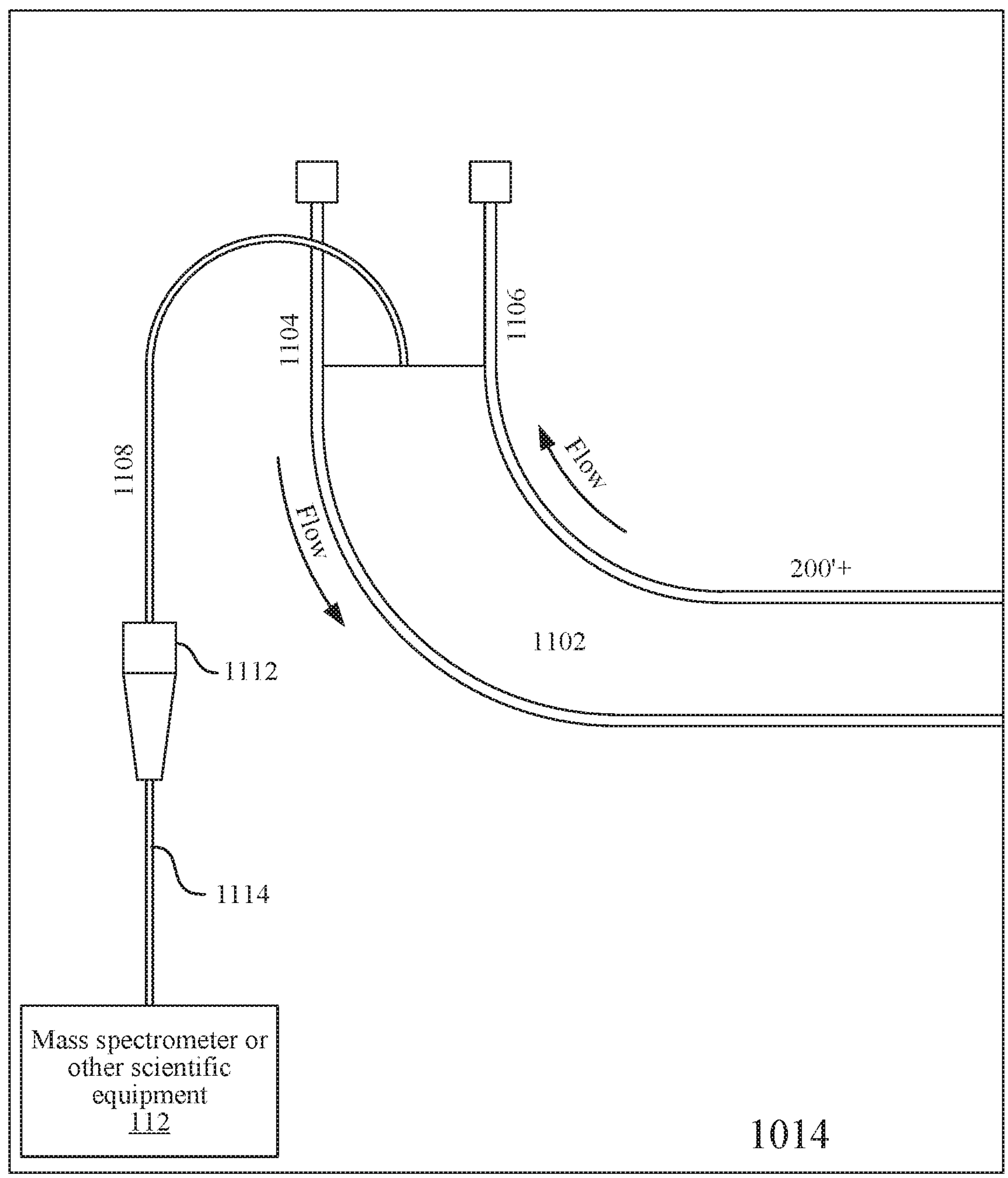

In some examples, a heavy steam-traced bundled hose is connected to the heat transfer loop 1000 in the cargo area, as illustrated in FIG. 11 in more detail. The heavy steam-traced bundled hose 1102, which may be the same as or incorporate one or more aspects of heat transfer loop 1000, may contain, in some aspects three PFA tubes (for example, as illustrated and described in reference to FIG. 8 above) in direct contact with one another to facilitate maximum heat transfer. These tubes may be surrounded by insulation material. The insulation is shrouded by a urethane jacket. Two of the PFA tubes are process tubes 1104, 1106, which run the liquid coolant in opposite directions from and to the primary coolant system. The third tube in the center is a tracer tube 1108, also known as an air inlet sampling tube. The two process tubes 1104, 1106 will heat the sampled air in the tracer tube 1108 at a high and constant temperature above ambient. As illustrated in FIG. 11, the tracer tube 1108 is connected in the cargo area 1014 with a color coded and lock controlled female quick-disconnect, attached directly to a mass spectrometer 112, or similar scientific instrument, via a coupler 1112 (e.g., ⅜ 10¼ inch) and a ¼" or ⅜" teflon tube 1114. One of the process tubes 1104 in the cargo area is connected to auxiliary heat transfer hose through a color-coded and lock controlled female quick-disconnect. This process tube connects with the upper heater hose. The other process tube 1106 in the cargo area is connected to the auxiliary heat transfer hose through a color-coded and lock controlled female quick-disconnect. This process tube 1108 connects with the lower heater hose. The liquid coolant in the process tubes 1104, 1106 may run in opposite directions to one another and can be continuously recycled through the primary coolant system at constant temperature. This helps ensure a constant temperature, or a minimum temperature, is provided adjacent to the tracer tube 1108.

Figure 12:
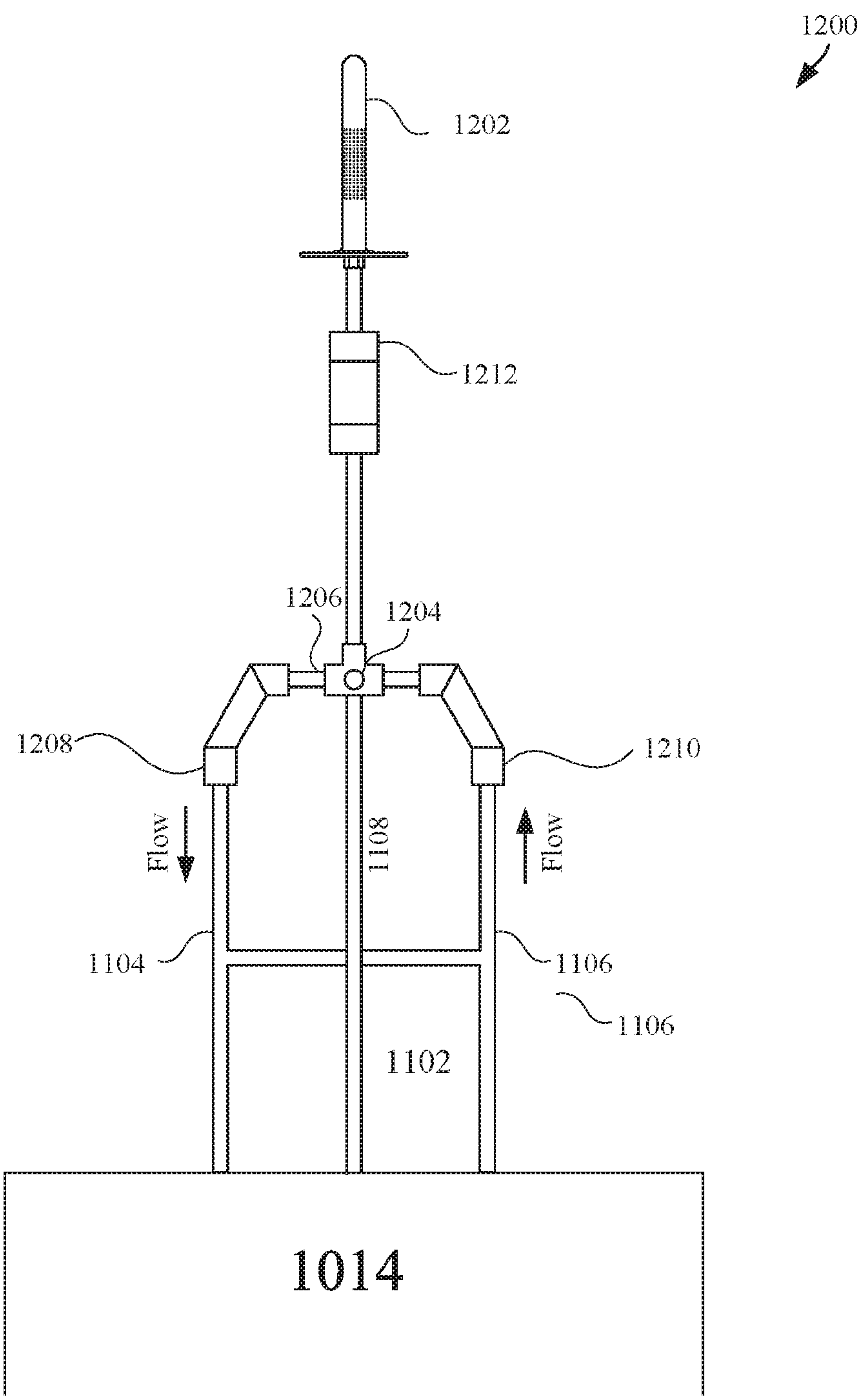
FIGS. 12 and 13 illustrate example auxiliary heat exchange systems that can be coupled to one or more sample or vapor collectors.

In some aspects, as illustrated in FIG. 12, at the terminal end of the tracer tube 1108 of the heat transfer loop 1000, 1102, the tracer tube 1108 is connected to a vapor collector or sampling device (filtering device) 1202, also called the Atomic/Molecular Vapor Collector (AMVC, described and discussed below). The two process tubes 1104, 1106 are connected to one another via "T" connector 1206 to permit the recirculation of liquid coolant back to the primary coolant system. A ⅜ths inch air relief valve 1204 is attached to a ⅜ths female tee 1206 to permit the purge of any air in the process tubes 1104, 1106. In some aspects, near the terminal end of bundled hose 1102, process tubes 1104, 1106 may converge via 45 degree compression elbows 1208, 1210 (e.g., ⅜" on ¼" compression 45 degree street elbow having ⅜" male threads) and connect to each other via tee connector 1206. In some aspects, a connector 1212 (e.g., a ⅜" on ¼" compression union) may removably couple the collector 1202 or a tube connected to the collector 1202 to the tracer tube 1108.

Figure 13:
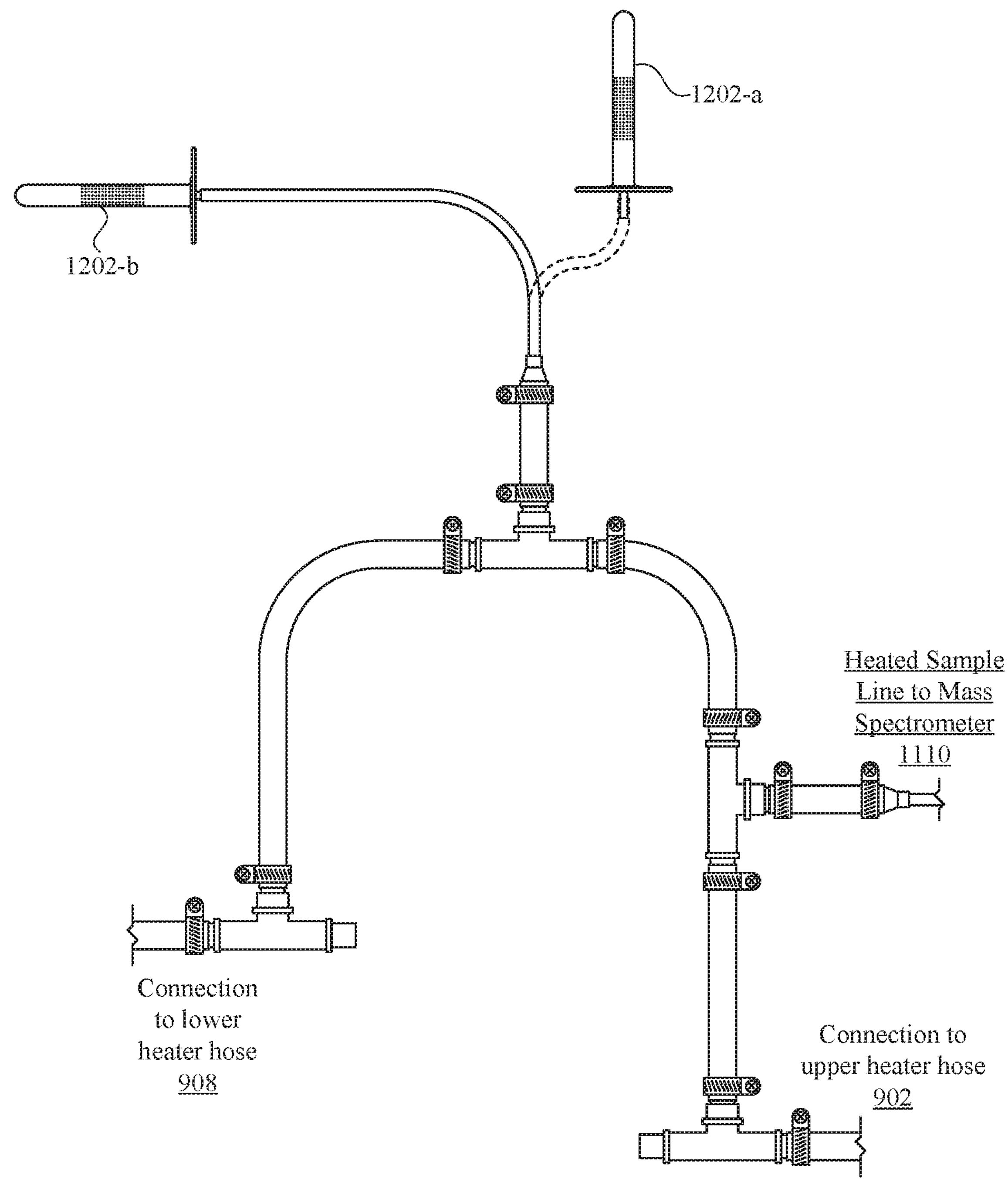

In yet another example, multiple vapor collectors or sampling devices, such as 1202-*a*, 1202-*b* or more, may be attached to an end of the tracer tuber, as illustrated in FIG. 13. In this example, one or more vapor collectors 1202-*a* may be coupled to tracer tube 1108, which may be exposed outside of hose bundle 1102 a short distance, when, for example, the ambient air is warm or hot. In this situation, to ensure that the transport temperature of the sample collected does not drop below the ambient temperature of the sample, the tracer tube 1108 should not be exposed for an extended length or distance outside of the hose bundle 1102/process tubes 1104, 1106. One or more vapor collectors 1202-*b* may additionally or alternatively be coupled to tracer tube 1108, which may be exposed outside of hose bundle 1102 a longer distance, when, for example, the ambient air is cooler or cold. In this example, it is not as critical to warm the tracer tube, as there is less likelihood that the sample will drop further in temperature before entering the hose bundle 1102.

The hotter the air sample is in the mass spectrometer, for example, over the ambient air sampled, the sharper peaks and better defined identification of organic and inorganic compounds thus results. Consequently, the inherent, significant, and long term problems of condensation contamination in air monitoring are eliminated with the AHE.

Applications of AHE are numerous. By reducing or substantially eliminating condensate contamination, AHE can be reliably used: to sample air quality in various extreme environments; to identify human remains in shipping containers; to detect drugs and explosives; to monitor organic (and inorganic) emissions in the auto, aerospace, coal, oil, and fracking industries; to monitor organic vapors emitted by humans for medical, pharmaceutical, and veterinary applications in disease detection and drug efficacy studies; and to determine spoilage and infections in agricultural products, essentially anywhere precise air or gas measurements are required and where condensate contamination is undesirable.

The length of the bundled hose may vary according to implementation. For example, a 200-foot length of the above described heat exchange system tubing may maintain constant temperatures of 155 degrees Fahrenheit in the air sample line. Lengths greater than 200 feet may require an auxiliary pump to recirculate coolant in the process tubes. In these instances, this auxiliary fluid pump, powered by a 12-volt battery or 110-volt power source, would be located close to the junction of the auxiliary and primary closed loop hoses in the engine compartment. Any coolant can be used in the system, but propylene glycol is preferred, due to its environmentally safe and excellent heat transfer qualities. Similarly, the heavy heat-traced bundled hose is preferred for use in AHE. The process and/or tracer tubes used in the AHE preferably contain the properties of high purity PFA tubing, like Zeus Corporation which claims, "High Purity PFA (HP PFA) exceeds the stringent requirements of the SEMI F57 specification. The unique molecular structure of HP PFA reduces chemical extractables, protects against ionic contamination, and is nonreactive with virtually all chemicals. HP PFA also has a maximum working temperature of 500° F. (260° C.), low gas permeability, and is flame resistant. In the semiconductor and pharmaceutical industries, HP PFA tubing is used for fluid handling applications requiring an extremely low level of chemical extractables. The product reduces metallic contamination and is designed to provide longer service life in the challenging semiconductor clean room environment. HP PFA is also used in applications that require a high continuous service temperature. Its qualities include excellent lubricity, clarity, flexibility, temperature and chemical resistance. This versatility has led to PFA being a popular material selection in the semiconductor, chemical, pharmaceutical and medical industries." Any tubing with these qualities will work with heavy steam-traced hoses for the AHE, like, but not limited to PFA, PEEK, or PTFE, etc. Also, due to different total lengths used in AHE applications, it may be advisable under certain pressures to utilize a high temperature backflow preventer in the lower heater hose, thus ensuring unimpeded flow and recirculation of the coolant throughout the primary and auxiliary systems. Finally, connections to the primary cooling system can occur at any point, such as the upper and lower radiator hoses, for example.

The AHE is well suited for air monitoring and sampling collection using mobile platforms, such as the mobile scientific platform, as described above, and permits analytic laboratories to become mobile and field deployed.

Other, inferior products may attempt to use electric heat tape, or heat strips, or heat-traced bundled hoses to eliminate condensation contamination. However, this approach does not work well for long lengths of the sampling tube. Additionally, the energy requirements to heat long lengths of hose are daunting –30 to 50 amps at 120 volts. In addition, it does not take in to consideration extreme temperature differences in ambient and measured air samples. Finally, the electric wires used for heat transfer are prone to breakage.

Figure 14:
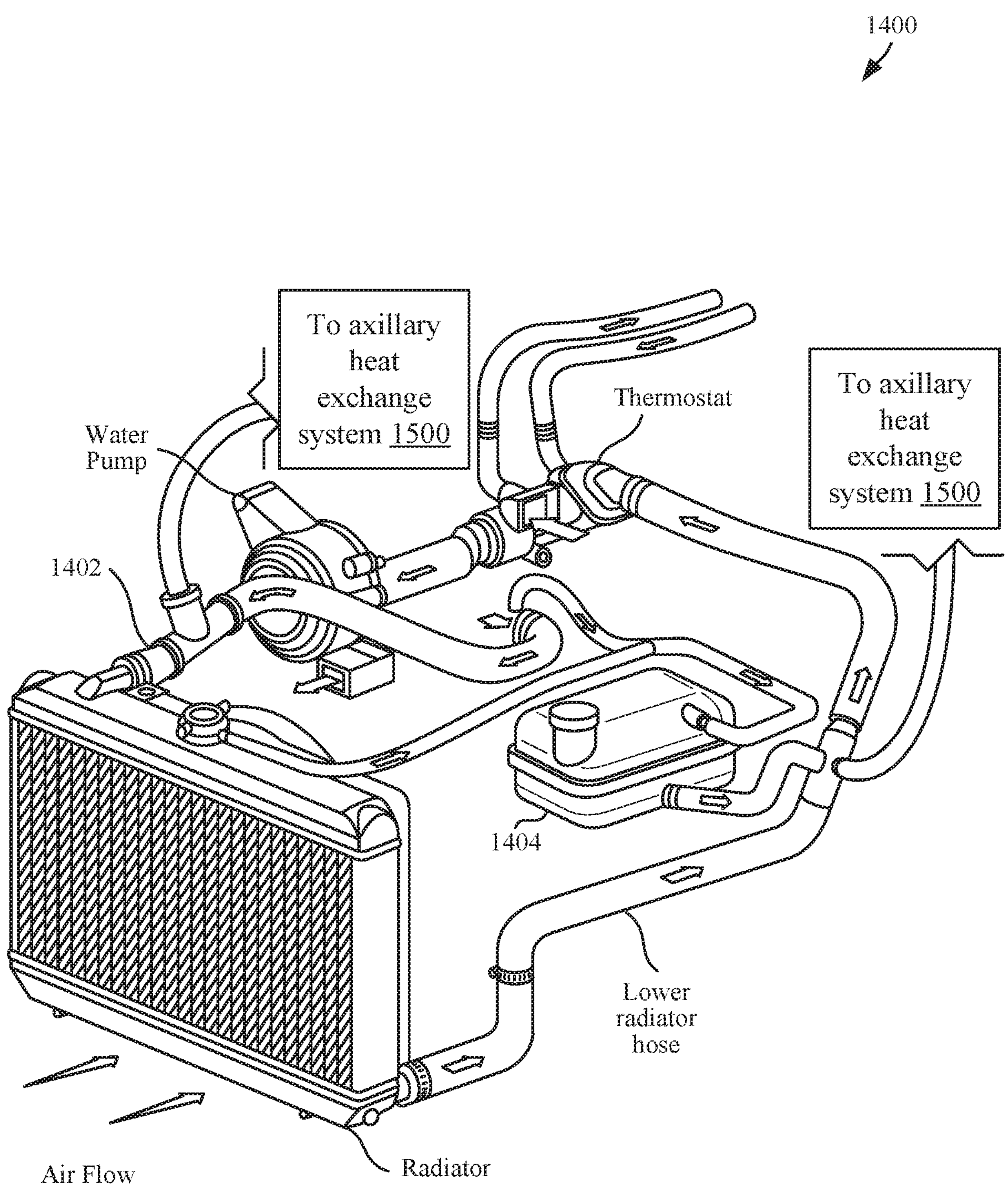
FIG. 14 illustrates another example cooling/heating system of a combustion engine to which an auxiliary heat exchange system may be coupled.
Figure 15:
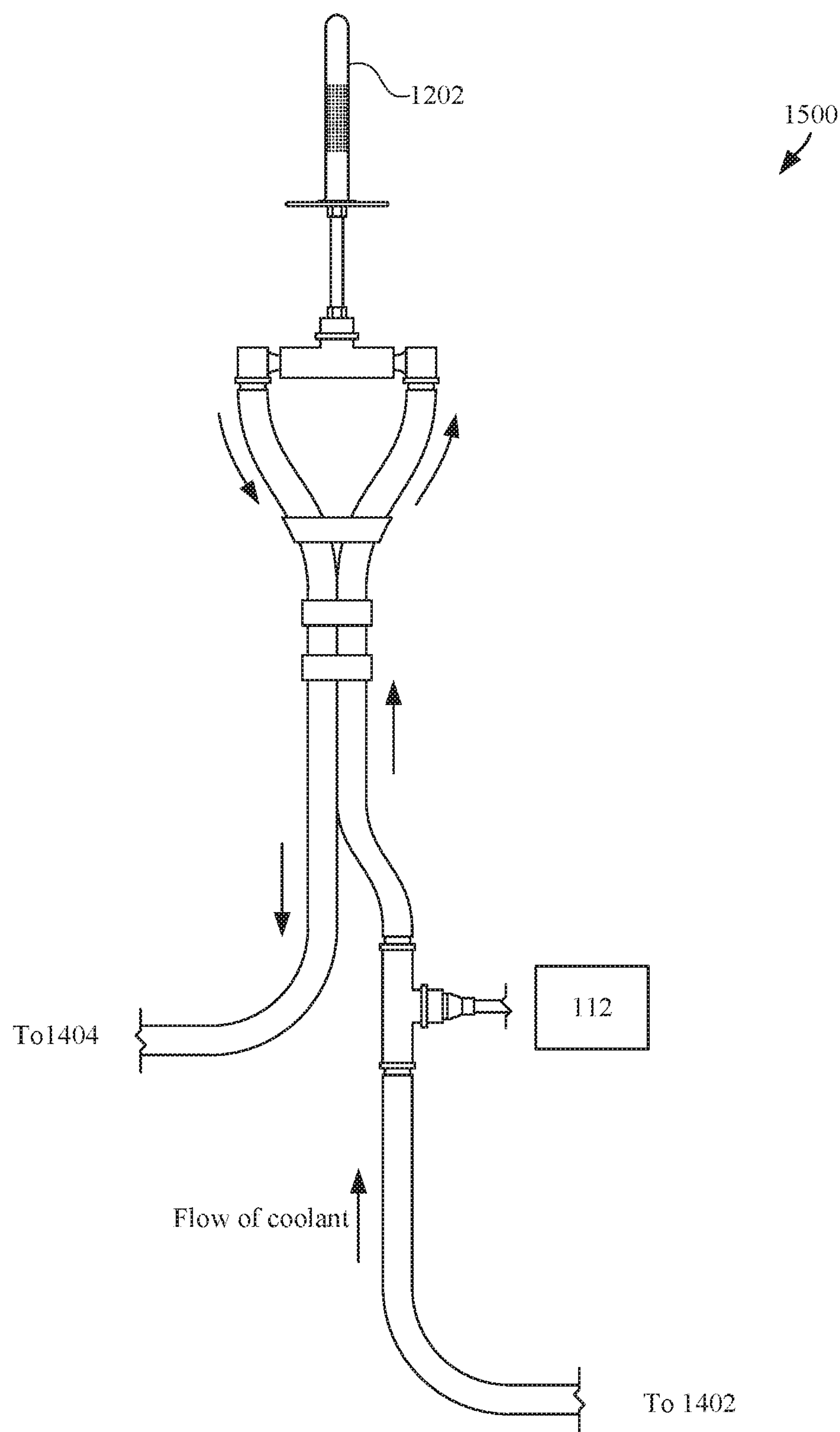
FIG. 15 illustrates another example auxiliary heat exchange system that can be coupled to one or more sample or vapor collectors.

Another example of an auxiliary heat exchange system 1500 is illustrated in FIG. 15. Auxiliary heat exchange system 1500 may be coupled to a recycling cooling/heating system 1400, as part of a combustion engine, as illustrated in FIG. 14. System 1400 may include one or more aspects of heating/cooling system 900 described above. In accordance with one embodiment, a suitable heat exchanger may be in the form of a tube-in-a-hose, or TIAH. TIAH is a device or system for eliminating the contamination of condensates in air sampling collection tubes and scientific measuring equipment by using heat exchange from closed coolant systems in internal combustion engines (gasoline, diesel, steam, natural gas, hydrogen, or propane) as well as any electrical engines in which waste heat is generated. A secondary supplemental closed heat exchange hose is employed to passively heat air inside of an inserted inlet tube used for air sampling to eliminate condensate contamination. System 1500 may include one or more aspects of the auxiliary heat exchange system described above in reference to FIGS. 8-12, and as a result, those features will not be again discussed here.

The heat exchange system 1500 may include a secondary closed heat transfer loop is attached to the primary cooling system 1400 at the upper radiator hose 1402 and may terminate in the coolant expansion tank 1404 associated with the engine in the mobile platform vehicle. Inside a section of the secondary circulating system 1500 is an inlet sampling tube at constant or increasing temperature from the terminal end of the inlet sampling tube (which may be connected to a sample collector 1202) to the scientific equipment used (e.g., 112), thus eliminating condensation of the air sample.

TIAH may be connected to any open or closed system of air or liquid heating/cooling. The secondary closed heat transfer loop can be teed in to the hottest part of the primary cooling system (typically between 80 to 100 degrees centigrade) using insulated high temperature hose, commonly found in automotive radiator hoses. Hose clamps would be used to secure the primary and secondary hose connections to prevent leakage of the coolant at the teed junction. In this particular example a ⅜th or ½ inch diameter radiator hose can be used for the secondary closed heat transfer loop. The inserted air inlet collection tube can be made of Ultra High Purity Teflon (or PTFE or PEEK), or any similar tubing in sizes ranging from ¼ to ⅜th inch diameter. The air inlet collection tube needs to be smaller than the secondary closed loop heat transfer hose. Upstream from the junction of the primary and secondary closed heat transfer hoses, the secondary hose is cut and a brass or similar metal barbed tee fitting is inserted and secured with hose clamps to prevent coolant leakage. The tee-fitting also has a compression fitting to attach the inlet air sampling tube, also to prevent leakage. The inlet air sampling tube is inserted in a section of the secondary closed heat transfer hose to any desired length and attached and secured as previously described.

As similarly discussed with reference to auxiliary heat exchanger above, for very long lengths of air inlet tubing, an auxiliary fluid pump may be required on the secondary closed heat transfer hose. In these instances, an auxiliary fluid pump, powered by a 12-volt battery or 110-volt power source, would be located close to the junction of the secondary and primary closed loop hoses. The hotter portion of the closed secondary heat transfer loop would be the preferred junction for the air inlet sampling tube, attached directly to a mass spectrometer, or other scientific instrumentation. Although propylene glycol would be the preferred medium used in the heat transfer process, ethylene glycol, water, or a combination thereof can be used, as well as only air. Ambient air sampled by an atomic/molecular vapor collector (AMVC) at the terminal end of the air inlet sampling tube will always be equal to, or slightly cooler than, the sample in the air inlet sampling tube, which is connected to the scientific equipment. Because the terminal end of the air inlet sampling tube will run opposite the flow of the heating/coolant direction in the secondary closed heating transfer tube, there will not be a drop of temperature in the air sample running to the scientific equipment. In fact, it may be slightly hotter. The hotter the ambient air sample is above the temperature going in to the mass spectrometer, for example, the sharper peaks and better defined identification of organic and inorganic chemicals thus results. Consequently, the inherent, significant, and long term problems of condensation contamination in air monitoring are eliminated or at least substantially reduced to the point of being inconsequential.

Applications for TIAH are numerous—wherever the elimination of condensate contamination is desired for air or gas sampling. For example, TIAH may be reliably used: to sample air quality in various extreme environments; to identify human remains in shipping containers; to detect drugs and explosives; to monitor organic emissions in the auto, aerospace, coal, oil, and fracking industries; to monitor organic vapors emitted by humans for medical, pharmaceutical, and veterinary applications in disease detection and drug efficacy studies; and to determine spoilage and infections in agricultural products.

Sample Vapor Collector

Figure 16:
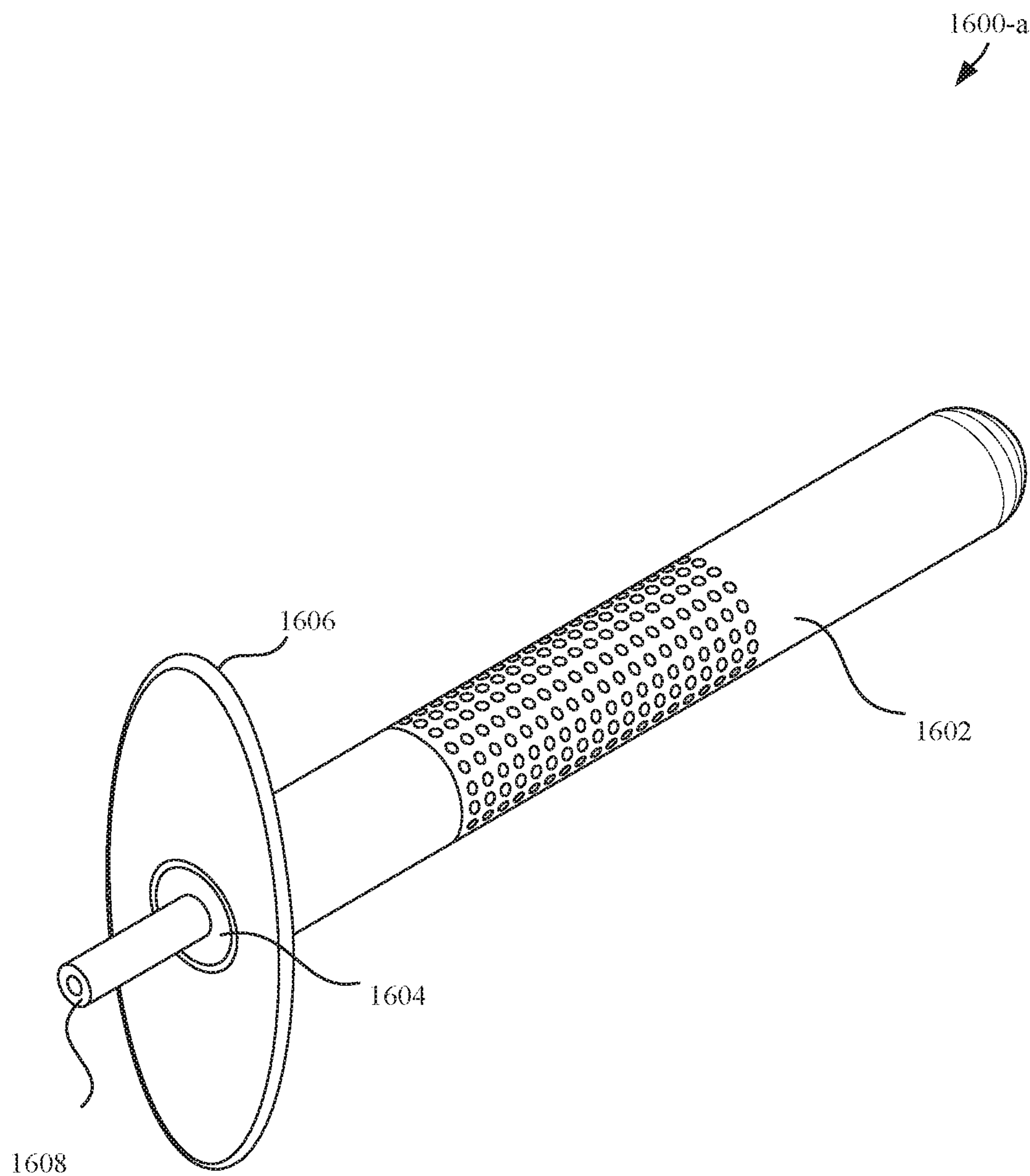
FIGS. 16-18 illustrate perspective views of an example sample or vapor collector, which may be used in conjunction with a mobile scientific platform and/or an auxiliary heat exchange system.
Figure 17:
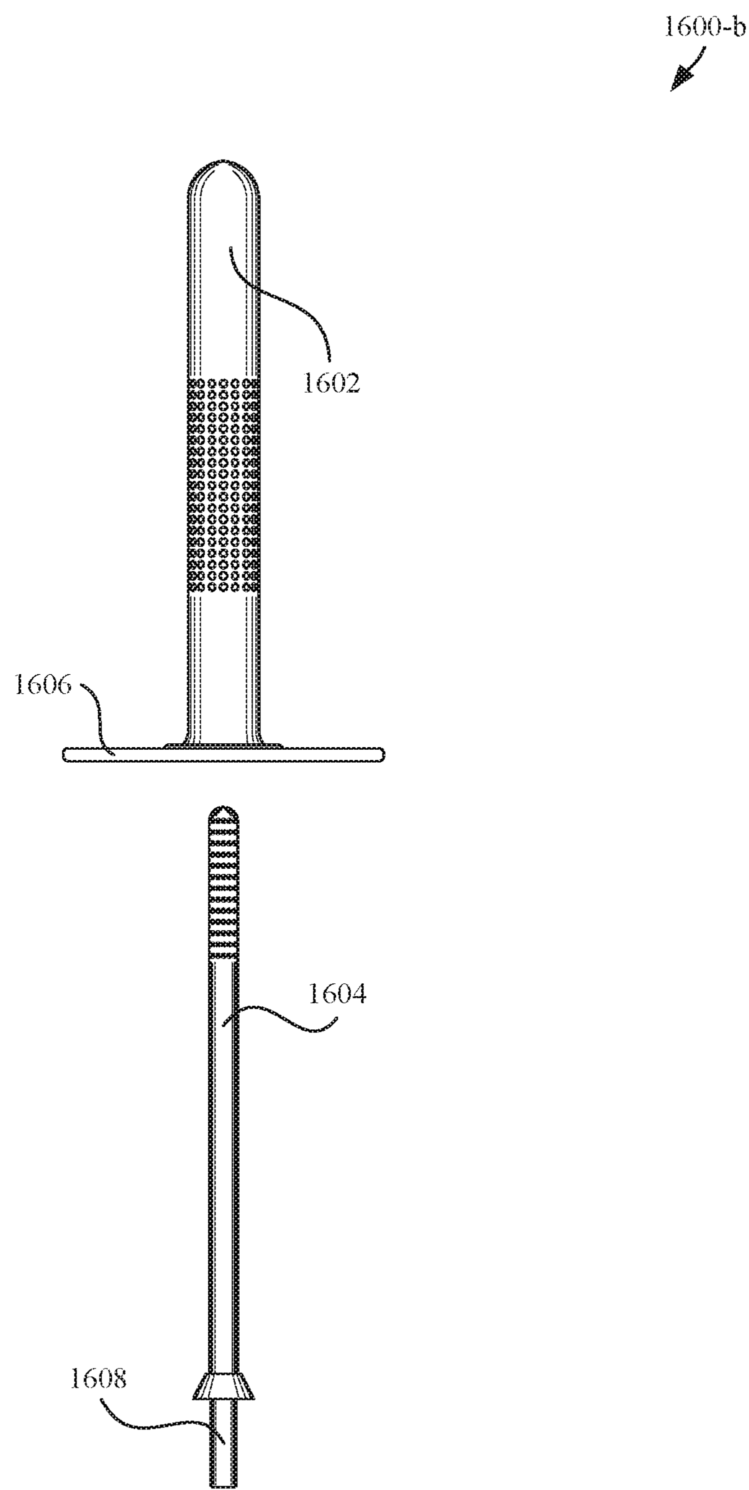
Figure 18:
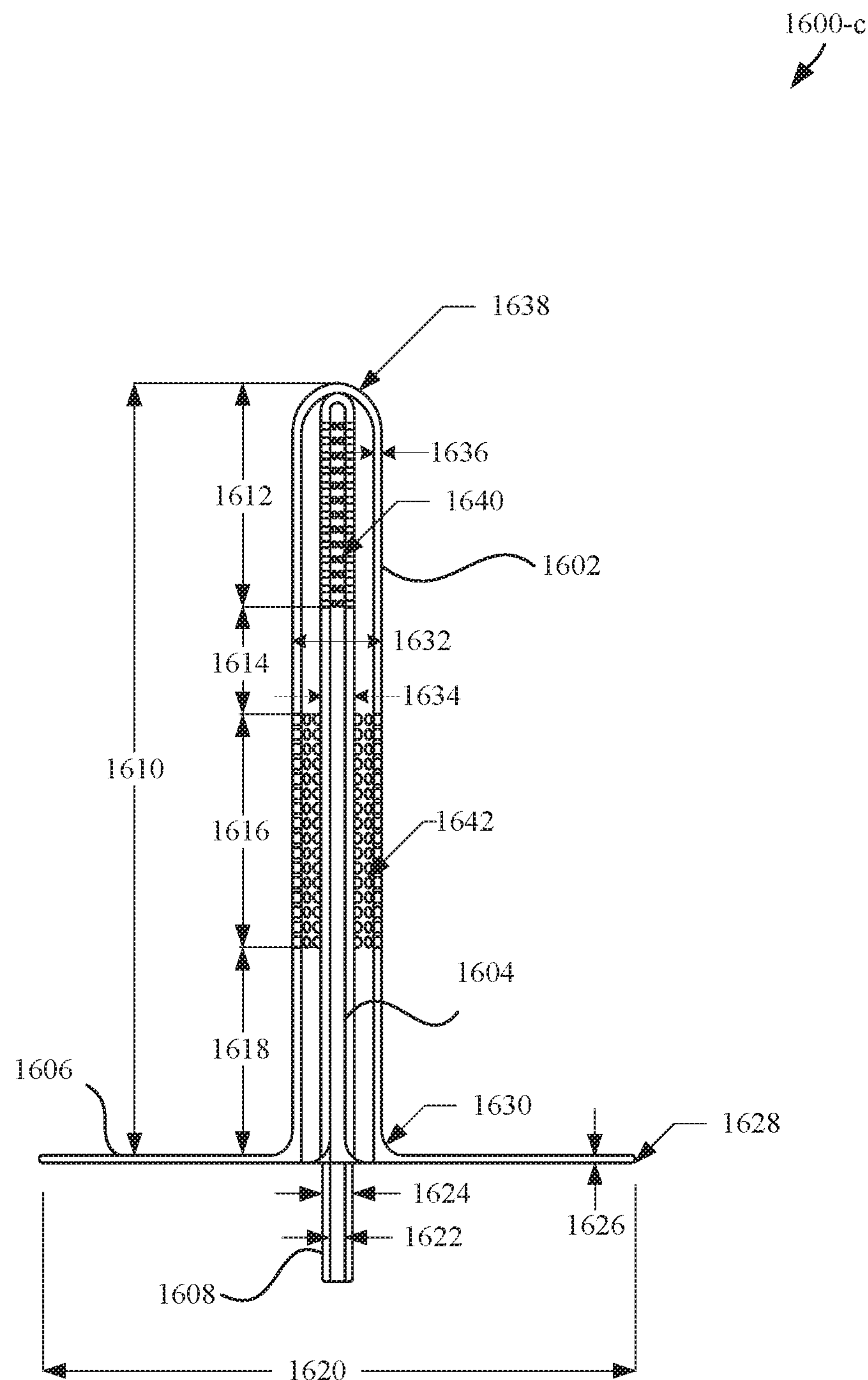

As illustrated in FIGS. 16-18, a sample collector or an atomic/molecular vapor collector (AMVC) is now discussed. In accordance with an embodiment, the described AMVC has applications for medical, pharmaceutical, environmental, energy, aerospace, drug enforcement, automotive, explosive detection, geological, mining/mineral/gas/oil exploration, toxic waste site, forensic, agricultural, scientific, research, and veterinary applications.

In some aspects, the described AMVC may be used for capturing atomic particles, molecular vapors of VOCs, (volatile organic chemicals), and/or inorganic chemicals, in air, liquids, and solids.

Commercial applications for AMVC include, but are not limited to: environmental testing, mobile laboratories (such as SciArk or SciLab, for example), rapid medical screening for viral, bacterial, viroid, and prion infections in plants, animals, and humans, heavy metal exposures in humans, human trafficking deterrence, physiological health determinations, metabolic disorders, cancer detection, drug detection and efficacy studies, analytic lab procedures, soil contamination, geological surveys, atmospheric testing, soil measurements, environmental air sampling, air quality measuring, and explosives identification. Some of its potential uses include research facilities, mobile laboratories (SciArk or SciLab), doctor's offices, hospitals, food and fragrance industries, veterinary clinics, outpatient facilities, surgical centers, blood banks, clinical laboratories, medical and veterinary schools, public health departments, morgues, as well as for agencies, such as, for example, WHO, EPA, FBI, DOJ, ICE, CIA, NSA, NTSB, NTSB, NOAA, NASA, CDC, and NIH, FEMA, DoD, DHS, DEA, Fire and Police Departments, and state/local environmental/public health agencies—wherever and whenever an uncontaminated source of uncondensed air (using, for example AHE as described above) is required for testing, monitoring, diagnosis, analysis, or evaluation of atomic particles and volatile organic (or inorganic) chemicals in air, liquids, or solids.

Prior approaches to (non-medical) air sampling have been plagued by sample contamination, condensation of organic, inorganic, and atomic elements in the sample lines or in the mass spectrometer, or other scientific instrumentation used, and the incorrect use of various mass spectrometers to analyze the air samples. A sample line with no AMVC (or AHE) is universally used.

As previously mentioned, the applications of AMVC are numerous, including various applications in which it is desirable to sample atomic and molecular vapors with an uncontaminated source of uncondensed air for testing, monitoring, diagnosing, analyzing, or evaluating the quality of air in any sampled source.

The described AMVC captures atomic elements and volatile organic or inorganic chemicals in air, liquids, or solids. In medical, veterinary, and pharmaceutical applications, AMVC captures molecular and atomic compounds emanating from different body cavities (stomach, lungs, rectal, nasal, vaginal, bladder, liver, etc.) in humans and animals for qualification and quantification in various mass spectrometers and other analytic devices. As such, it can be used as an adjunct to, or a replacement for, other conventional tests (i.e., blood, tissue samples, surgeries, biopsies, etc.) that take time to analyze, are expensive, and have invasive consequences, like iatrogenic and nosocomial infections. With AMVC, real time, immediate results are obtained when connected to appropriate mass spectrometers or other analytic devices.

In the energy, geological, aerospace, and environmental arenas, the described AMVC may be used to collect volatile organic or inorganic chemicals and atomic elements to detect soil, air, and solid contaminations, such as lead in city water supplies.

In the drug detection area, AMVC (when connected to appropriate mass spectrometers or other scientific instruments) may be used to determine the presence of illicit substances in shipping containers or semi-trucks.

In explosive detection, the air sampled by AMVC (when connected to appropriate mass spectrometers or other scientific instruments) may be analyzed to detect the presence of various explosive compounds at airports, bus/train/shipping terminals, stadium events, and other mass gatherings.

In the agricultural industry, the described AMVC (when connected to appropriate mass spectrometers or other scientific instruments) may be used to detect the presence of spoilage and pathogens to the food supply in warehouses, shipping containers, store shelves, and the like.

Additional applications of AMVC include breath analysis for the detection of metabolic disorders, diseases, and cancers in humans. In these applications, patients may exhale into a collection tube (such as AMVC) and the collected vapors may then be analyzed in appropriate mass spectrometers or other scientific instruments. This may initially obviate the need in some instances for more invasive medical procedures. As such, it can be used for immediate medical screening for infectious diseases, metabolic disorders, physiological health, heavy metal contamination, and cancers, to name a few. Also, the AMVC can replace the need for more invasive procedures, like colonoscopies, bronchoscopies, endoscopies, catheterizations, etc.

Prior approaches in breath analysis research in the medical, veterinary, pharmaceutical industries have relied exclusively on exhaled vapors from lungs in humans and animals. That approach involves the assumption that atomic and molecular elements under investigation found in the patient's blood will be extracted from a liquid medium to a vapor state through gas exchange in the alveoli of the lungs and collected for analysis on exhalation without contamination for evaluation and validation using appropriate analytic instruments. Most metabolic processes occur in organs below the lungs (liver, stomach, pancreas, kidneys, etc.), which eventually empty in to the intestines and bladder. As such, sampling vapors from these locations are more predictive of various infections, metabolic disorders, and heavy metal contaminations. Moreover, all atomic and molecular materials have different volatilities. Volatility is the property of a substance to vaporize from a liquid to a gaseous state. Volatility is also influenced by temperature, pressure, size of the element under investigation, and chemical/nuclear bonds with other organic and inorganic compounds. Sublimation, on the other hand, is when a solid transitions directly to a gaseous phase without being converted to a liquid as an intermediate step. Both volatility and sublimation of atomic and molecular elements vary significantly from species to species, the body cavities from which the vapors are sampled, and the particular elements under investigation. Here and in other industries, prior efforts did not stop detritus and liquids from entering the collection line and eventually in to the scientific instrumentation used for air analysis. The described AMVC addresses these one or more of these problems.

FIGS. 16-18 illustrate various perspective views 1600-*a*, 1600-*b*, and 1600-*c* of an AMVC device 1600, as described herein. According to one embodiment, AMVC is in the form of a rigid or flexible, disposable, sterile, and/or reusable device can be made of varying lengths and thicknesses and is preferably composed of Ultra High Purity Teflon (PFA), PEEK, PTFE, or passivated stainless steel. Other materials can be used (like, latex, nitrile, rubber, graphene, glass, metal, or other poly carbonate materials), for example, when the VOCs or inorganics emitted by these materials do not interfere, contaminate, or compromise the measurements in the mass spectrometer, or other analytic instrumentation. The device may be designed and constructed to have no moving parts and may be inexpensive to mass-produce as a sterile device. The described AMVC device enables clinicians and researchers to capture atomic and molecular vapors from various locations that have previously been untested. AMVC obviates the need in some instances for more invasive initial medical procedures. As such, it can be used for mobile and real-time medical screening for infectious diseases, metabolic disorders, physiological health, heavy metal contamination, and cancers, to name a few. Also, the device can replace the need for more invasive procedures, like colonoscopies, bronchoscopies, endoscopies, catheterizations, etc., the described AMVC can also be attached to any sampling line which is connected to an appropriate mass spectrometer or other scientific instruments for environmental, agricultural, explosive detections, drug identification, geological, atmospheric, etc. air sampling uses. The rigid version of the AMVC can be mounted to rail, aircraft, ships, and other mobile platforms, such as the mobile scientific platform described above, and/or used in conjunction with the AHE and TIAH, also previously described.

According to one embodiment, AMVC (filtering device) comprises four parts, all fabricated into one piece or device, which may be inserted in to various body cavities (colon, vagina, stomach, bladder, lungs, liver, nose, mouth, ears, etc.) for vapor sampling. An outer vapor collector 1602 may be a hollow tube with perforations of various sizes toward the bottom or a first end of the collector. Its purpose is to collect organic or inorganic vapors while screening out detritus like urine, feces, blood, and other body fluids and secretions, or other objects or particles found in air or gas samples (e.g., dust, leaves, rain, and so on). An inner vapor collector 1604 captures the same air without the associated detritus. It has perforations of various sizes at the top or end opposite the first end of the outer collector 1602, so no detritus enters the hollow tube. The top of inner vapor collector 1604 is preferably molded or affixed (e.g., rigidly attached) to the top of the outer vapor collector for stability. In some examples, all or most of the perforations on the inner vapor collector 1604 may be located above the perforations on the outer vapor collector 1602 (e.g., no overlapping when the collector 1600 is placed in a vertical orientation). A saddle 1606, which may be formed or attached to a second end of the outer collector 1602 (opposite the first end), may prevent the AMVC from being inserted beyond the desired length. A hollow collection tube connector 1608 allows a vacuum collection tube to be attached to a mass spectrometer or other analytic device to quantify and qualify the atomic, volatile organic vapors, and/or inorganic compounds collected. In some aspects, the collection tube connector 1608 may be attached to the base of the inner vapor collector 1604, and may have a dimeter that enables attachment to a vacuum line. This vacuum line is typically the air sampling line which leads to an appropriate mass spectrometer, like the PTRMS, GC-MS, or MALDI-MS, or other analytic devices to quantify and qualify the vapors collected.

Various dimensions, 1610-1642, are illustrated in FIG. 18. It should be appreciated that the values of these dimensions, as will be described below, are only given as an example. One or more of the dimensions may be changed, and still be considered within the scope of this disclosure. For example, length 1610 and saddle width 1620 may be modified according to an intended use of the collector 1600. In other examples, the number of, sizing, and relative position (in the vertical direction as shown) of perforations of the inner tube and outer tube may be selected according to an intended use of the collector, such as bigger and more holes may be used in the outer collector to filter out larger objects or detritus, whereas smaller holes may be selected for smaller detritus, etc. In some aspects the difference 1614 between the position of the perforations of the inner and outer tubes may be selected based on a desired air flow or number of samples to be taken in a given time period. In other cases, the perforations may be positioned to overlap. The width 1632 of the outer tube 1602 may be selected based on the size of aperture or average size of an aperture that the device is to be inserted for collecting gas samples. These design criteria are only given by way of example; it should be appreciated that other design modifications, based on any number of factors, are contemplated herein.

As illustrated, the following dimensions may have the following values, as detailed in the following table:

| | |
|---|---|
| 1610 | 6½" |
| 1612 | 1⅞" |
| 1614 | 29/32" |
| 1616 | 2" |
| 1618 | 1½" |
| 1620 | 5" |
| 1622 | ⅛" |
| 1624 | ¼" |
| 1626 | 1/16" |
| 1628 | R .3" |
| 1630 | R 7/32" |
| 1632 | ¾" |
| 1634 | 9/32" |
| 1636 | 1/16" |
| 1638 | R 13/32" |
| 1640 | 1/32" |
| 1642 | 3/32" |

It should be appreciated that these values may increase or decrease by a small or larger percentage, be measured in other units, and so on.

The described AMVC may be cleared of detritus after insertion in the body cavity through positive air flow in the collection tube connector 1608. Additionally, radioactive isotopes, luminescents, dyes, stains, enzymes, and other effluents can be introduced in to the selected body cavities through the collection tube connector 1608 to enhance the identification and analysis of atomic and molecular vapors under investigation through the use of mass spectrometers and other analytic technics as discussed herein.

According to an alternative embodiment, the described AMVC can be used or manufactured without a saddle, such as if the lengths are identified and calibrated on the outer vapor collector. Consequently, AMVC can be adjusted for various sizes of human and animal subjects (i.e., adults versus children and giraffes versus gerbals), as well as modified for other enclosed environments. Additionally, the device can be used in conjunction with or incorporated in to other medical devices, like endotracheal and nasogastric tubes, catheters, etc. When used in concert with these devices, the AMVC can be inserted inside. as a further alternative embodiment, the saddle can be modified in to a handle. The collection tube adapter can be replaced with a male threaded fitting, or the beveled end of the inner vapor collector can be bored to a female thread. for liquid sampling, the above description (in which all perforations on the inner vapor collector must always be located above the perforations on the outer vapor collector) hold true, except that the perforations in the outer and inner vapor collector would need to be reversed when the AMVC is inverted in to a liquid.

Various additional features and implementations of the described vapor collector are described below.

In one aspect, a system or device for the collection of atomic elements and molecular compounds may include four primary parts or components, for example, all fabricated or formed in to one device, for vapor sampling. The sampling device may include an outer vapor collector, which may be a hollow tube with perforations of various sizes toward the bottom whose purpose is to collect atomic and molecular vapors while screening out detritus like urine, feces, blood, body fluids, secretions, as well as other environmental contaminants. The sampling device may additionally include an inner vapor collector, which captures the same air without the associated detritus with perforations of various sizes at the top only, so no detritus enters the hollow tube, where the top of the inner vapor collector is molded or affixed to the top of the outer vapor collector for stability. In some cases, all or most of the perforations on the inner vapor collector must always be located above the perforations on the outer vapor collector. In yet some cases, a saddle may prevents the device from being inserted beyond the desired length, and may be attached to one of the outer vapor collector. In some aspects, a hollow collection tube connector allows a vacuum collection tube to be attached to an appropriate mass spectrometer or other analytic device to quantify and qualify the vapors collected.

In one aspect, the described sample or vapor collector may be part of a system for the sampling of air in various body cavities (colon, vagina, stomach, bladder, lungs, liver, nose, mouth, ears, etc.) of animals and humans, as well as other enclosed environments, for analysis by appropriate (static, mobile, portable, or hand held) mass spectrometers and other analytic devices, as described above. The described sample or vapor collector may be used in a system for the detection of heavy metals and other trace elements in the (Atomic) Periodic Table from various body cavities (colon, vagina, stomach, liver, bladder, lungs, nose, mouth, ears, etc.) of animals and humans. The described sample or vapor collector may also be used for detecting materials in other enclosed environments, including, but not limited to the detection of environmental exposures to atomic elements like lead, mercury, copper, arsenic, etc., where: a rapid, reliable, and immediate detection of elements can be qualified and quantified for appropriate medical, veterinary, agricultural, and environmental interventions, and/or where a source point location can be identified for epidemiological and public health investigations, like the recent Flint water crisis with lead poisoning. It should also be appreciated that a fixed measurement platform could also be implemented with the described sample or vapor collector and/or the auxiliary heat exchange system, and be within the scope of the present disclosure.

In one aspect, the described sample or vapor collector may be part of a system for the detection of organic molecular compounds and molecular fragments from various body cavities (colon, vagina, stomach, bladder, lungs, nose, liver, mouth, ears, etc.) of animals and humans, as well as other enclosed environments, for analysis by appropriate analytic devices, including, but not limited to the detection of bacteria, viruses, prions, viroids, virions, fungi, molds, yeasts, DNA and RNA strands, explosives, and drugs. These systems, using the described sample or vapor collector, may enable the rapid, reliable, and immediate detection of infectious viral diseases like, but not limited to Zika, Ebola, West Nile, malaria, Hanta, norovirus, dengue and yellow fever, syphilis, virions, and cancers. These systems, using the described sample or vapor collector, may further enable the rapid, reliable, and immediate detection of infections bacterial diseases like, but not limited to *streptococcus, staphylococcus, Escherichia coli, meningitis, gonorrhea, chlamydia, Eukaryotic, Prokaryotic*, and parasitic infections, etc. It should also be appreciated that a fixed measurement platform could also be implemented with the described sample or vapor collector and/or the auxiliary heat exchange system, and be within the scope of the present disclosure.

Figure 19:
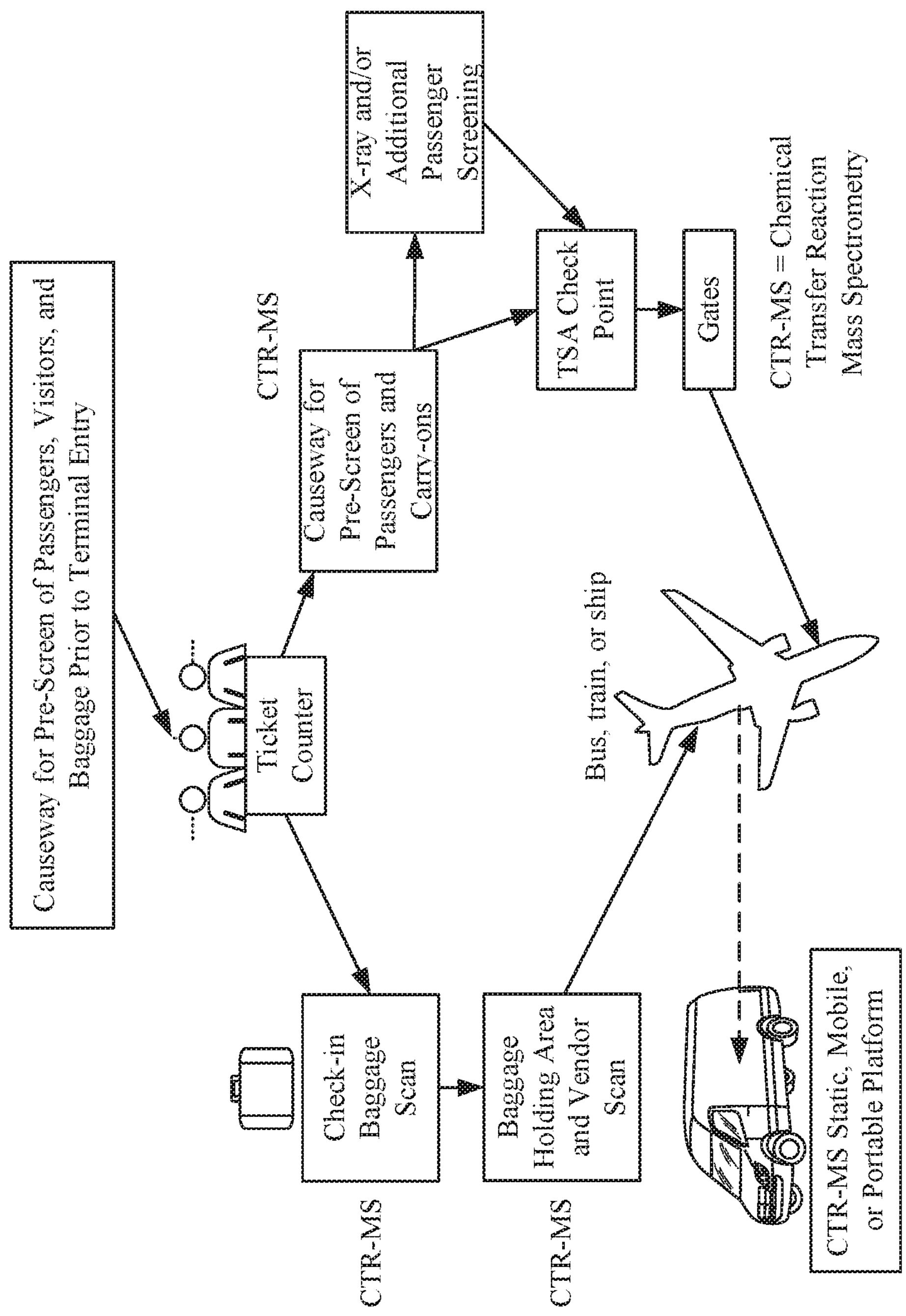
FIG. 19 illustrates one example implementation of the sample or vapor collector of FIGS. 16-18.

In another example, as illustrated in FIG. 19, the described sample or vapor collector may be used in a system to detect explosives, such as TATP, DAPT, TNT, SEMTEX, etc. at airports (pre-terminal or terminal), train, bus, ship, stadium events, and where ever large mass gatherings occur. As illustrated, some or all causeways (pre-terminal and terminal locations) may have AMVC devices installed in the walls, floors, and/or ceilings. In some aspects, the mobile scientific platform, either in mobile form (e.g., integrated into a vehicle), or as a transportable unit (e.g., in a container or trailer), may be used to analyze data collected by the one or more sample or vapor collectors. In yet some aspects, the auxiliary heat exchange system may also be utilized to help provide contaminate free samples to the mobile scientific platform. It should also be appreciated that a fixed measurement platform could also be implemented with the described sample or vapor collector and/or the auxiliary heat exchange system, and be within the scope of the present disclosure.

Figure 20:
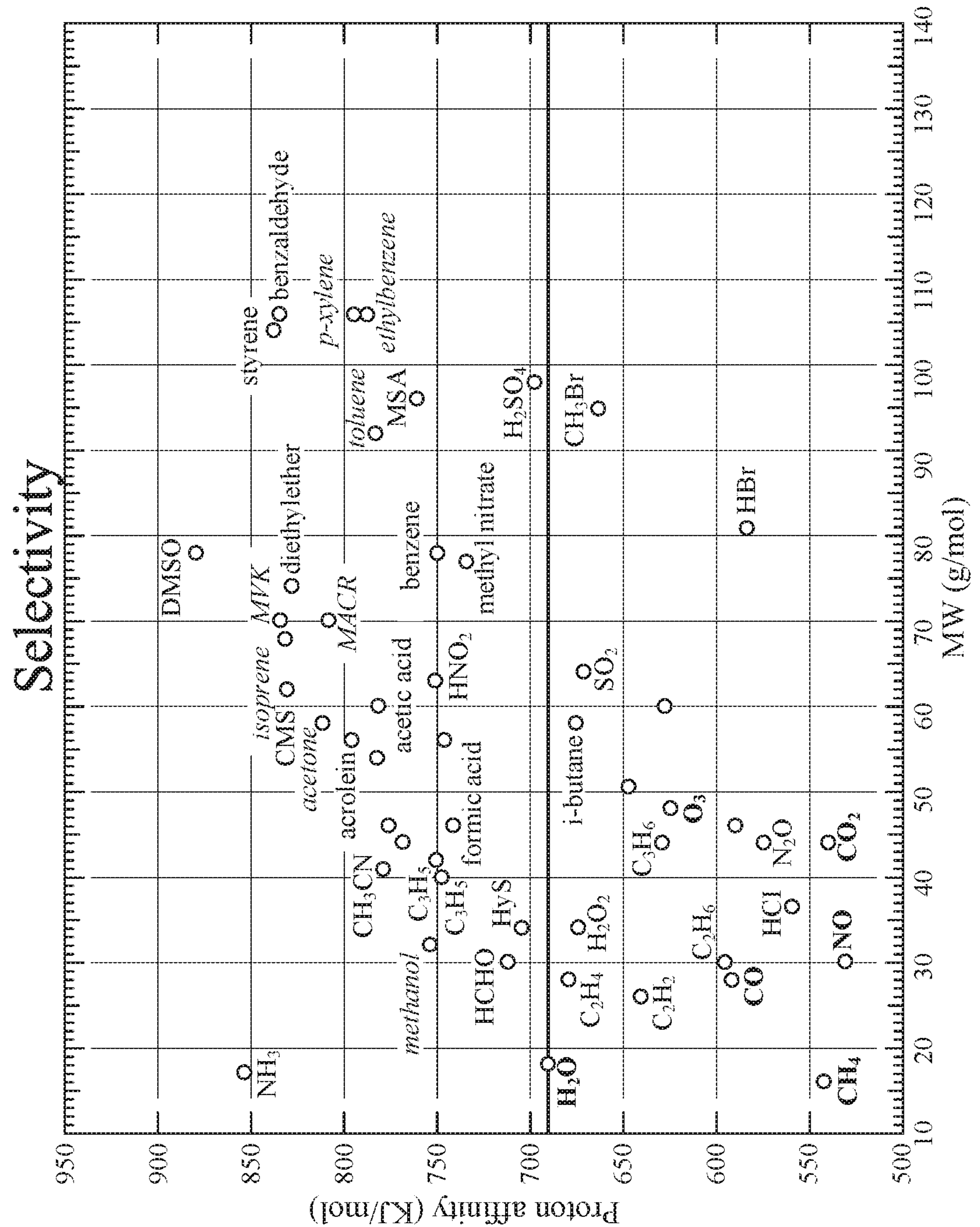
FIGS. 20-25 illustrate example sampling results obtained using the sample or vapor collector of FIGS. 16-18.
Figure 21:
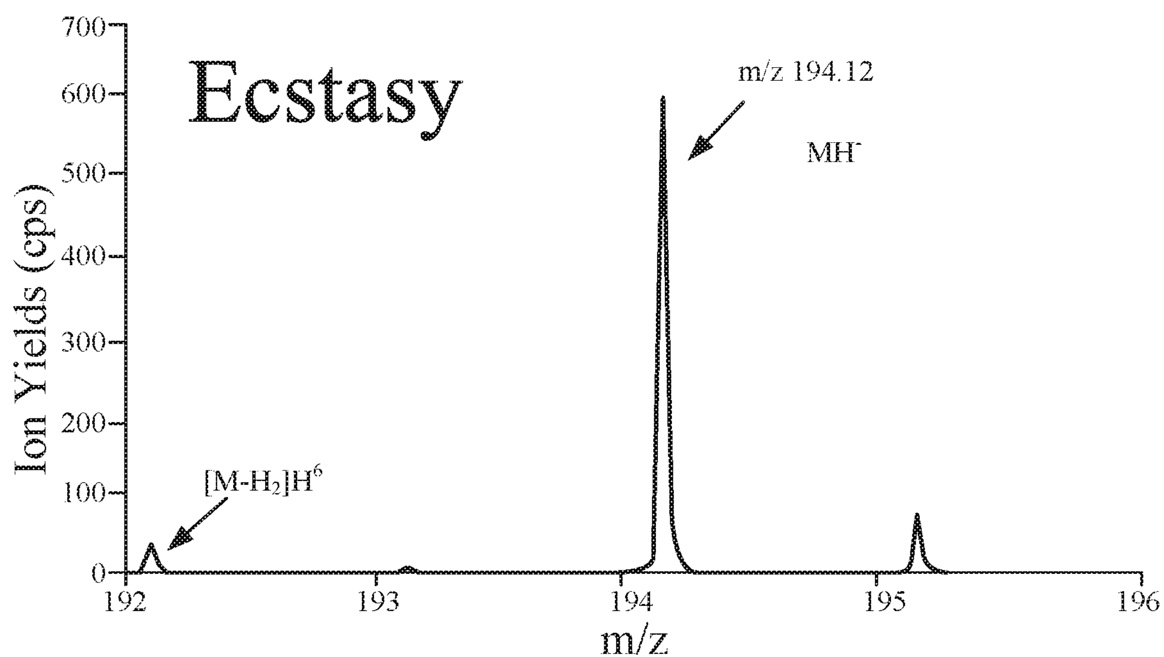
Figure 22:
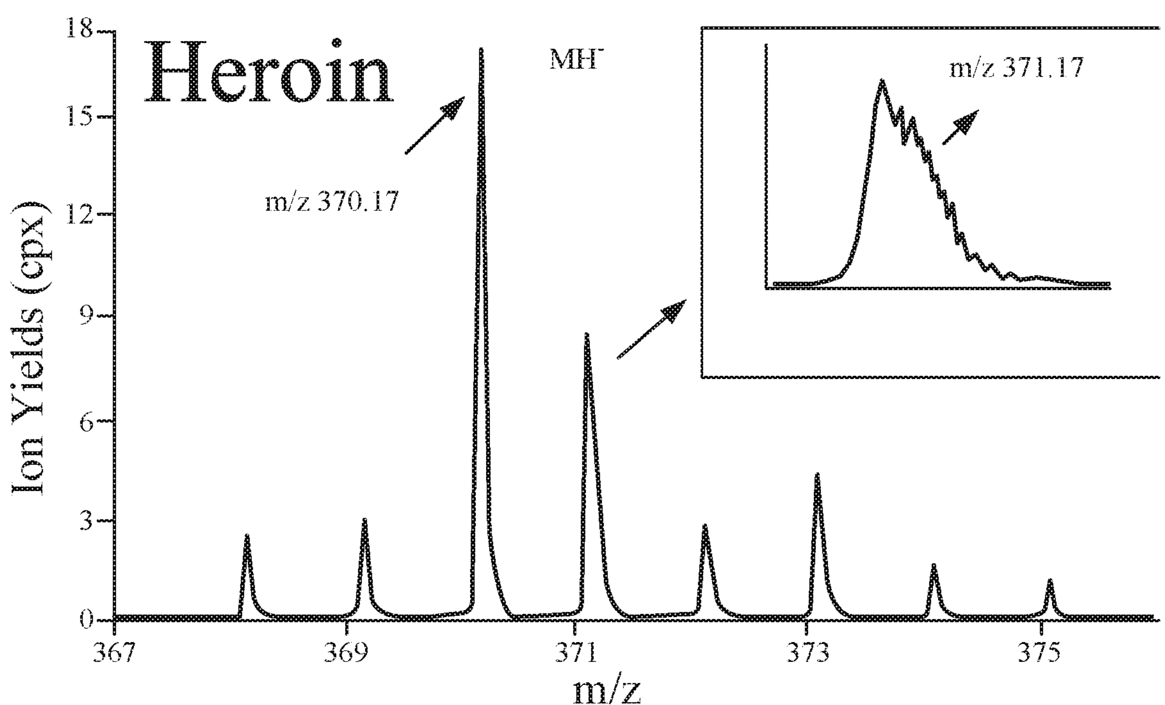
Figure 23:
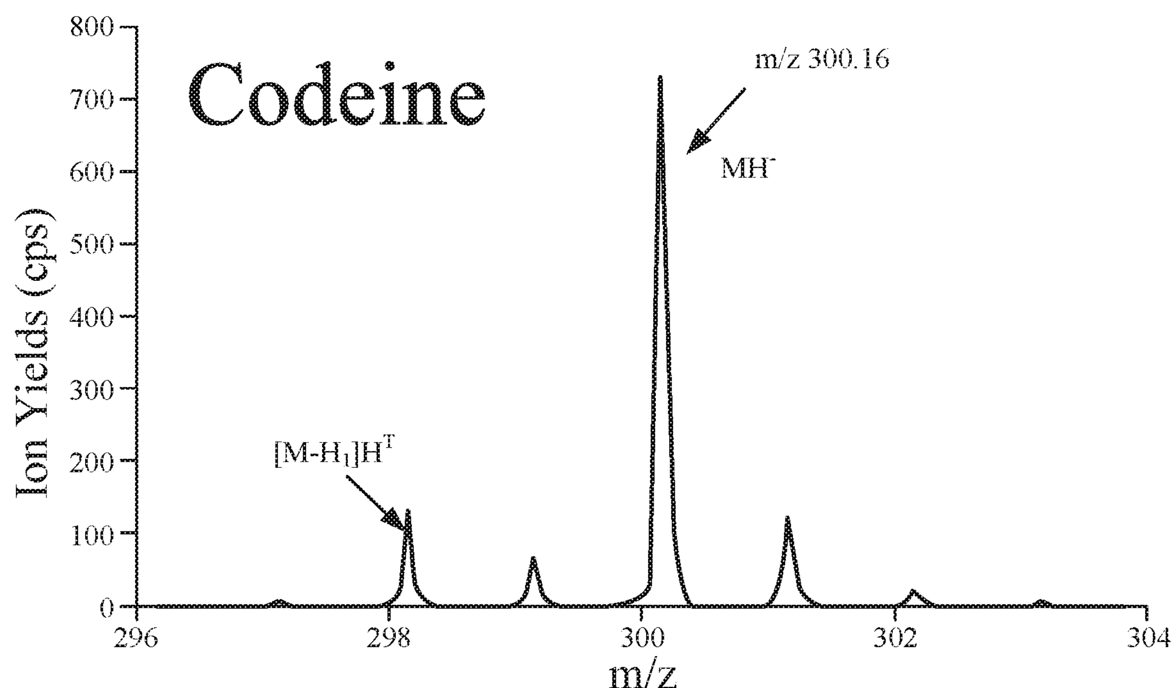
Figure 24:
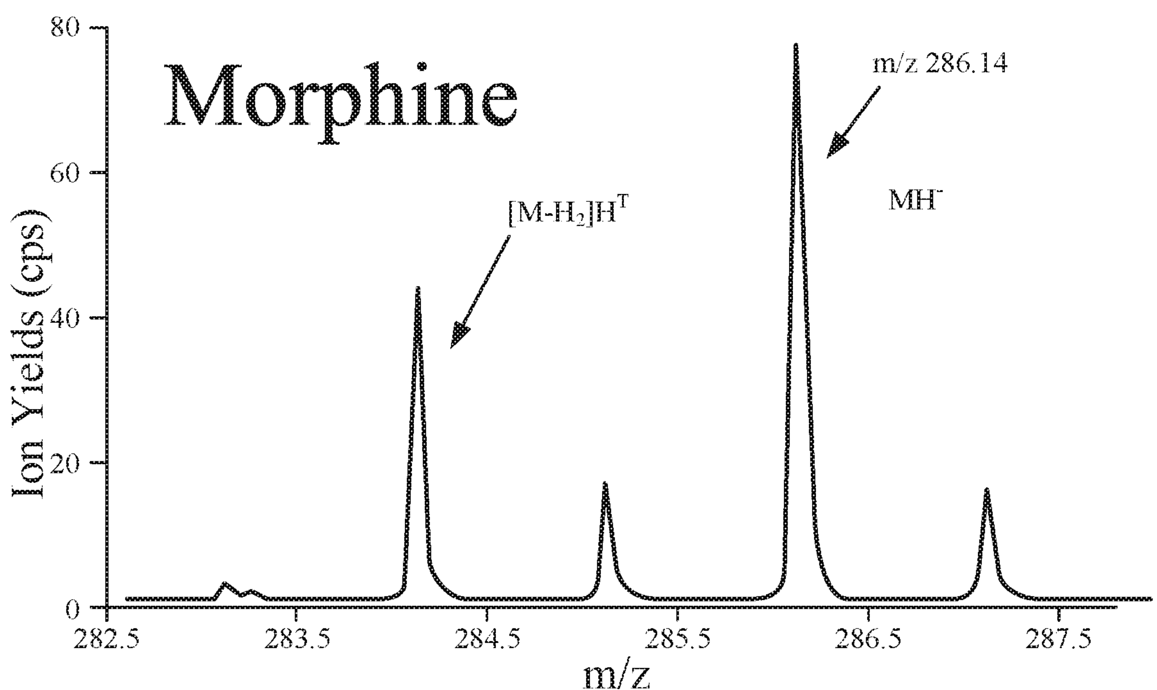
Figure 25:
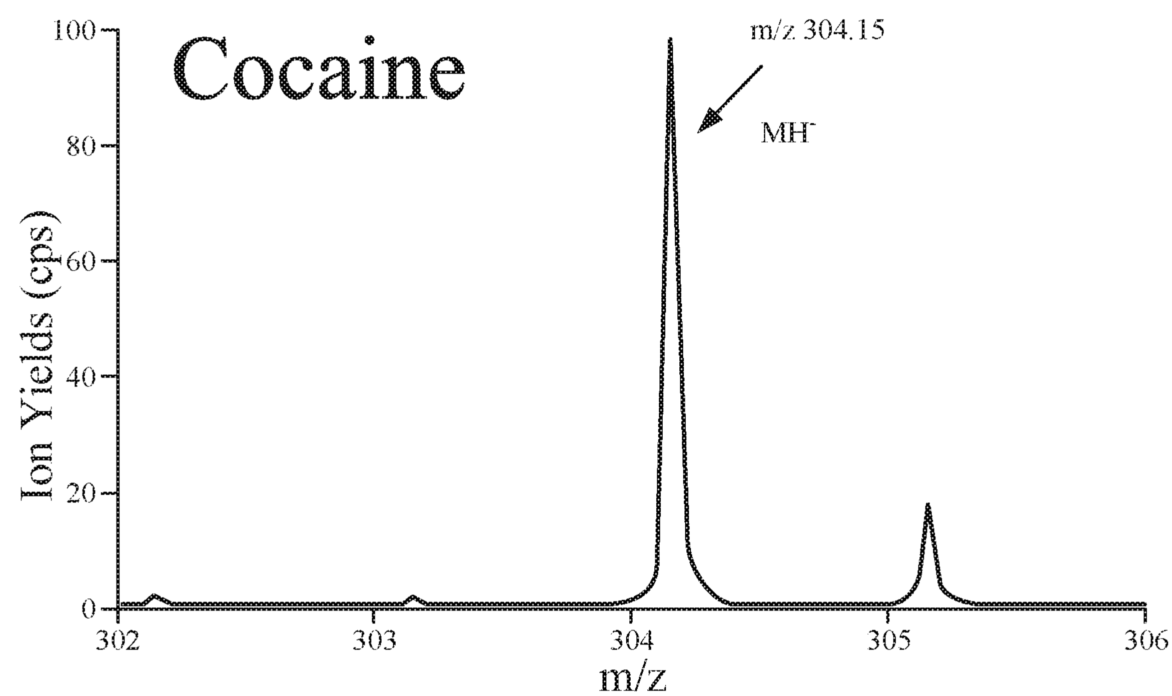

The described sample or vapor collector may be used in a system to detect a variety of drugs, such as heroin, ecstasy, fentanyl, codeine, methamphetamine, cocaine, and other precursors used in the manufacture of illicit substances and in prescription drugs, as well as the absorption, distribution, retention, metabolism, excretion, and efficacy of new and existing drugs in pharmacokinetic trials. The selectivity of various compounds, when collected by the described sample or vapor collector, and analyzed by a mass spectrometer, for example, is illustrated in FIG. 20. FIGS. 21-25 illustrate detection results of various illicit, prescribed, and recreational drugs, which may be obtained using the described vapor collector, auxiliary heat exchange system, and/or the mobile scientific platform, as described herein.

In yet one aspect, the described sample or vapor collector may be part of a system for measuring or otherwise helping to determine the time, rate, and severity of viral, bacterial, parasitic infections, or drug/explosive exposures through vapor sampling of various body cavities (colon, vagina, stomach, bladder, lungs, nose, mouth, ears, etc.) in animals and humans, as well as other enclosed environments. Samples may be collected using the described sample or vapor collector, and the ratio of infectious agents or environmental exposures to the host response in antibody production in the sample(s) may be determined. In some aspects, the operation of this type of system may include a qualification and quantification of the infectious agents or environmental exposures from vapor samples collected from various body cavities, as well as other enclosed environments. The operation of this type of system may further include a qualification and quantification of the host antibodies from vapor samples collected in various body cavities as a response to the infectious agents or environmental exposures. The operation of this type of system further include establishing a ratio of the infectious agents or environmental contaminants to the host antibodies produced, to then determine the type, time, rate, and severity of the infectious agents or environmental exposures for clinically appropriate medical, veterinary, or agricultural treatments, including drug, surgical, and other therapeutic interventions.

In yet one aspect, the described sample or vapor collector may be part of a system for the detection of volatile organic or inorganic compounds and molecular fragments from various body cavities (colon, vagina, stomach, bladder, liver, lungs, nose, mouth, ears, etc.) of animals and humans, as well as other enclosed environments, including, but not limited to aerobic and anaerobic bacteria emitted by cadavers over time, when compared to the different volatile organic or inorganic chemicals emitted by living humans and animals. In some aspects, the operation of this type of system may include a qualification and quantification of volatile organic or inorganic chemicals emitted at various times during the decay of human and animal cadavers. The operation of this type of system may further include a qualification and quantification of volatile organic chemicals emitted at various times by living humans and animals. A comparison of the volatile organic chemicals emitted by the living and dead (animals and humans) may then be performed for forensic investigations in to time of death and in the identification and location of humans and animals involved in illegal trafficking operations, for example.

In yet one aspect, the described sample or vapor collector may be part of a system for the detection of viruses, bacteria, molds, yeasts, and other pathogens in agricultural products. This may include a method to certify, in conjunction with the FDA and/or USDA, agricultural products in warehouses and shipping containers to be free of spoilage and organic, inorganic, or atomic contamination before shipping to ports of destination, using one or more aspects of the described vapor collector, auxiliary heat exchange system, and/or the mobile scientific platform. This may alternatively include a method to certify, in conjunction with the FDA and/or USDA the same shipment upon receipt of agricultural products at ports of entry using one or more aspects of the described vapor collector, auxiliary heat exchange system, and/or the mobile scientific platform.

In yet one aspect, the described sample or vapor collector may be part of a system for the qualification and quantification of environmental air quality, which may permit the certification of indoor environmental quality (IEQ) in homes, business, and industry in concert with the Leadership in Energy and Environmental Design (LEED), for example, as well as the US Green Business Certification Inc. (USGBCI) certification processes for volatile organic chemicals standards.

In yet one aspect, the described sample or vapor collector may be part of a system for the identification of soil contamination at superfund sites, which may include the measurement of atomic elements, inorganics, and volatile organic chemicals at ground level, and/or the measurement of atomic and volatile organic or inorganic chemicals at various depths of bore drillings.

In yet one aspect, the described sample or vapor collector may be part of a system for the identification of and location of fossil fuels and related minerals, as well as fracking byproducts in the energy sector, which may include the measurement of atomic and volatile organic or inorganic chemicals at various depths of bore hole drillings in land or water environments.

While various examples, aspects, features, and implementations of a mobile scientific platform, auxiliary heat exchange system, and a sample or vapor collector, and various combinations thereof, have been illustrated and described, as noted above, many changes can be made without departing from the spirit and scope of this disclosure. Accordingly, the scope of the disclosure is not limited by the specific examples described herein.

What is claimed is:

1. An auxiliary heat exchange system for use in gas sampling, the system comprising:

at least one first conduit housed in an external casing, wherein the at least one first conduit is removably attachable to a heating/cooling system of a vehicle, wherein the at least one first conduit forms a heat transfer loop with a heating circuit of the heating/cooling system of the vehicle;

a tracer conduit for transporting gas samples, wherein the tracer conduit is positioned proximate to the first conduit and housed in the external casing for at least a partial length of the at least one first conduit, wherein the tracer conduit comprises a first end removably attachable to a gas collection device and a second end removably attachable to a measuring device, the gas samples having a first temperature; and wherein the first conduit carries heated fluid at a second temperature higher than the first temperature from the heating/cooling system of the vehicle to maintain at least a threshold temperature of the gas samples in the tracer conduit to prevent or reduce formation of condensates in the tracer conduit.

2. The system of claim 1, wherein the at least one first conduit is made of PFA, PEEK, or PTFE.

3. The system of claim 1, wherein the tracer conduit is made of PFA, PEEK, or PTFE.

4. The system of claim 1, wherein the at least one first conduit is removably attachable to an inlet heating hose providing liquid to a heater core of the vehicle and an outlet heating hose providing liquid back to the heating/cooling system of the vehicle.

5. The system of claim 1, wherein the at least one first conduit is removably attachable to a radiator hose of the heating/cooling system and to a coolant expansion tank of the heating/cooling system of the vehicle.

6. The system of claim 1, wherein the at least one first conduit is removably attachable to an inlet heating hose providing liquid to a heater core of the vehicle and an outlet heating hose providing liquid back to the heating/cooling system of the vehicle.

7. The system of claim 1, wherein the at least one first conduit is removably attachable to radiator hose of the heating/cooling system and to a coolant expansion tank of the heating/cooling system of the vehicle.

8. The system of claim 1, wherein the threshold temperature is set to greater than the ambient temperature.

9. The system of claim 1, further comprising an auxiliary pump coupled to the at least one first conduit, wherein the pump is configured to move liquid through an extended length of the at least one first conduit.

10. The system of claim 1, wherein the vehicle comprises a mobile scientific platform.

11. The system of claim 1, wherein the gas collection device further comprises a two layered filtering device, wherein the two layers each have perforations, and wherein the perforations do not overlap.

12. The system of claim 11, wherein the two layers each form a tube that is closed at a common end.

13. The system of claim 1, wherein the at least one first conduit comprises a first conduit and a second conduit each positioned parallel to the tracer conduit in the external casing.

14. The system of claim 13, wherein the first conduit and the second conduit are in direct contact with the tracer conduit.

15. The system of claim 14, wherein the first conduit, the second conduit, and the tracer conduit are incased in water soluble chloride in absorption-resistant fibrous glass insulation.

16. The system of claim 15, wherein the external casing comprises a non-halogenated thermoplastic urethane and covers the absorption-resistant fibrous glass insulation.

17. An auxiliary heat exchange system for use in gas sampling, the system comprising:

a first conduit and a second conduit both housed in an external casing, wherein each of the first conduit and the second conduit are removably attachable to a heating system of a vehicle; wherein the first conduit forms a heat transfer loop with a heating circuit of the heating/cooling system of the vehicle;

a tracer conduit, having a first length, for transporting gas samples, wherein the tracer conduit is positioned proximate to the first conduit and the second conduit and housed in the external casing for at least a partial length of the first conduit and the second conduit, wherein the tracer conduit comprises a first end removably attached to a gas collection device and a second end removably attachable to a measuring device, the gas samples having a first temperature; and wherein the first conduit and the second conduit carry heated fluid at a second temperature higher than the first temperature from the heating/cooling system of the vehicle to maintain at least a threshold temperature of the gas samples in at least a majority of the length of the tracer conduit to reduce formation of condensates in the tracer conduit.

18. The system of claim 17, wherein the first conduit and the second conduit are in direct contact with the tracer conduit.

19. The system of claim 17, wherein the second conduit forms a heat transfer loop with the heating/cooling system of the vehicle.

20. The system of claim 17, wherein the at least one first conduit is removably attachable to an inlet heating hose providing liquid to a heater core of the vehicle and an outlet heating hose providing liquid back to the heating/cooling system of the vehicle.

21. The system of claim 17, wherein the at least one first conduit is removably attachable to radiator hose of the heating/cooling system and to a coolant expansion tank of the heating/cooling system of the vehicle.

22. An auxiliary heat exchange system for use in gas sampling, the system comprising:

at least one first conduit;

a connection fitting for removably attaching the at least one first conduit to a heating/cooling system of a vehicle; wherein the at least one first conduit forms a heat transfer loop with a heating circuit of the heating/cooling system of the vehicle;

a tracer conduit for transporting a gas sample, the tracer conduit comprising a first end adapted to be removably attached to a gas collection device and a second end adapted to be removably attached to a measuring device; and a casing surrounding at least a portion of the at least one first conduit and at least a portion of the tracer conduit;

wherein at least a partial length of the first conduit extends proximate the tracer conduit such that the gas sample within the tracer conduit may be maintained at a sufficient temperature to prevent or reduce formation of condensates.

23. The system of claim 22, further comprising a gas collection device and measuring device both attached to the tracer conduit.

24. An auxiliary heat exchange system for use in gas sampling, the system comprising:

at least one first conduit housed in an external casing, wherein the at least one first conduit is removably attachable to a heating/cooling system of a vehicle; wherein the at least one first conduit forms a heat transfer loop with a heating circuit of the heating/cooling system of the vehicle;

a tracer conduit for transporting gas samples, wherein the tracer conduit is positioned proximate to the first conduit and housed in the external casing for at least a partial length of the at least one first conduit, wherein the tracer conduit comprises a first end removably attachable to a gas collection device and a second end removably attachable to a measuring device, the gas samples having a first temperature; and wherein the first conduit is configured to carry heated fluid at a second temperature higher than the first temperature from the heating/cooling system of the vehicle to maintain at least a threshold temperature of the gas samples in the tracer conduit to prevent or reduce formation of condensates in the tracer conduit.

* * * * *